(12) United States Patent
Bistany et al.

(10) Patent No.: US 11,913,931 B2
(45) Date of Patent: Feb. 27, 2024

(54) VAPORIZED AEROSOL DETECTION NETWORK

(71) Applicant: Zeptive, Inc., Burlington, MA (US)

(72) Inventors: Loucinda C. Bistany, Methuen, MA (US); William D. Hargett, Chelmsford, MA (US); Stephen S. Milt, Winchester, MA (US)

( * ) Notice: Subject to any disclaimer, the term of this patent is extended or adjusted under 35 U.S.C. 154(b) by 0 days.

(21) Appl. No.: 17/314,851

(22) Filed: May 7, 2021

(65) Prior Publication Data

US 2021/0278387 A1 Sep. 9, 2021

Related U.S. Application Data

(63) Continuation-in-part of application No. 17/072,892, filed on Oct. 16, 2020, now Pat. No. 11,030,877.

(60) Provisional application No. 62/929,893, filed on Nov. 3, 2019.

(51) Int. Cl.
| | | |
|---|---|---|
| *G01N 33/00* | (2006.01) | |
| *F24F 11/56* | (2018.01) | |
| *F24F 11/88* | (2018.01) | |
| *F24F 11/72* | (2018.01) | |
| *F24F 120/10* | (2018.01) | |
| *F24F 110/62* | (2018.01) | |
| *F24F 110/20* | (2018.01) | |
| *F24F 110/10* | (2018.01) | |
| *F24F 110/64* | (2018.01) | |

(52) U.S. Cl.
CPC .......... *G01N 33/0065* (2013.01); *F24F 11/56* (2018.01); *F24F 11/72* (2018.01); *F24F 11/88* (2018.01); *G01N 33/0031* (2013.01); *G01N 33/0075* (2013.01); *F24F 2110/10* (2018.01); *F24F 2110/20* (2018.01); *F24F 2110/62* (2018.01); *F24F 2110/64* (2018.01); *F24F 2120/10* (2018.01)

(58) Field of Classification Search
CPC ........... G01N 33/0065; G01N 33/0031; G01N 33/0075; F24F 2110/10; F24F 2110/20; F24F 2110/62; F24F 2110/64; F24F 2120/10
See application file for complete search history.

(56) References Cited

U.S. PATENT DOCUMENTS

| | | | | |
|---|---|---|---|---|
| 2004/0257235 | A1* | 12/2004 | Right | F24F 11/49 |
| | | | | 340/514 |
| 2015/0310720 | A1* | 10/2015 | Gettings | G06F 16/113 |
| | | | | 340/540 |
| 2018/0340701 | A1* | 11/2018 | Baughman | G01N 33/0063 |

FOREIGN PATENT DOCUMENTS

| | | | | |
|---|---|---|---|---|
| CN | 103968881 | * | 5/2014 | |
| DE | 102018214936 | * | 9/2018 | ............... G08B 6/00 |

* cited by examiner

*Primary Examiner* — Hongmin Fan

(57) ABSTRACT

A distributed security system includes a detection unit disposed at a first location. The detection unit includes a particle sensor that is configured to detect a particle count in first location. The detection unit also includes a housing enclosing a portion of the particle sensor. The security system also includes a camera disposed at a second location and having a field of vision encompassing the first location. The camera is configured to capture a video of the first location. The system also includes a server communicatively connected to the detection unit and the camera and configured to associate the particle count with the video.

10 Claims, 14 Drawing Sheets

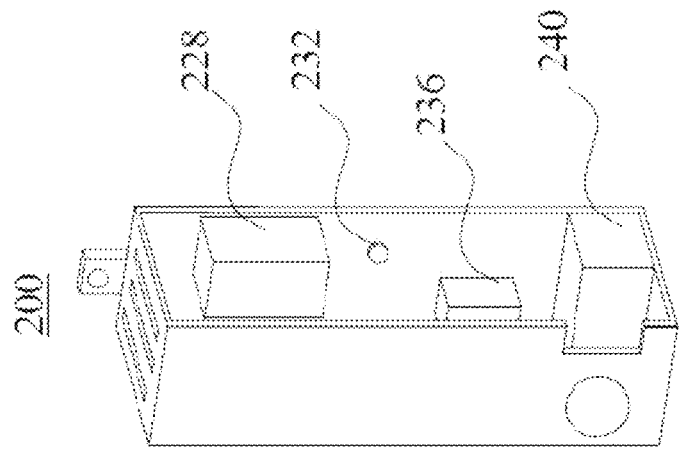
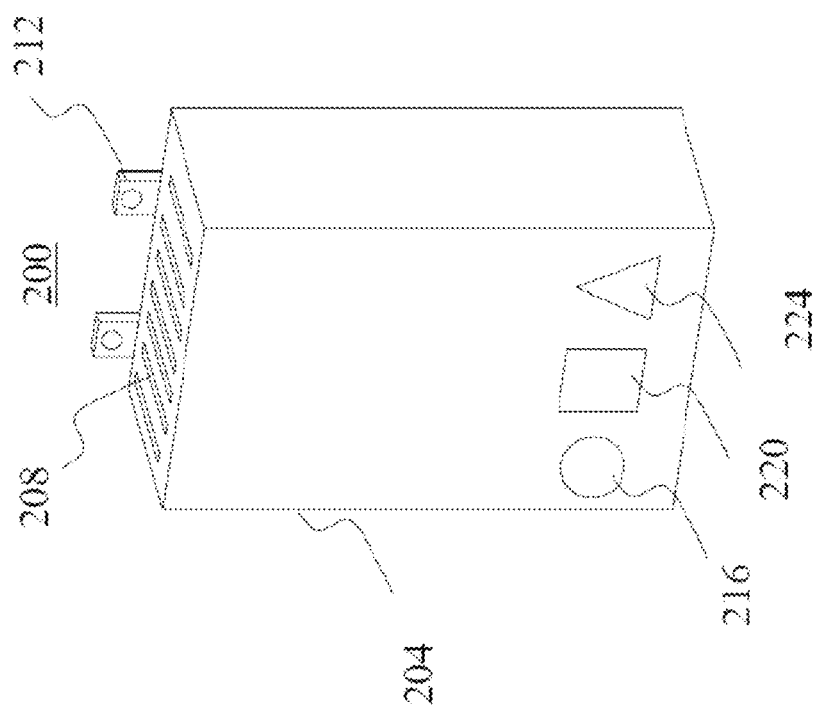
FIG. 2B
FIG. 2A

VAPORIZED AEROSOL DETECTION NETWORK

CROSS-REFERENCE TO RELATED APPLICATIONS

This application is a continuation-in-part of U.S. patent application Ser. No. 17/072,892 filed on Oct. 16, 2020 and entitled "Vaporized Aerosol Detection Network" which in turn claims the benefit of priority to U.S. Provisional Patent Application Ser. No. 62/929,893 filed on Nov. 3, 2019 and entitled "Distributed Cloud Enabled Device Network". Each above-referenced application is incorporated by reference herein in its entirety.

FIELD OF THE INVENTION

The present invention generally relates to the field of detection of vaporized aerosols. In particular, the present invention is directed to a system and method of sensors and signals to detect substances of interest and alert one or more users to its detection.

BACKGROUND

The proliferation of Electronic Nicotine Delivery Systems (ENDS) and Electronic Non-Nicotine Delivery Systems (ENNDS) requires the detection of the products of those systems in certain indoor areas and/or vehicles. Currently, some systems for the detection of vaporized aerosols are used in limited settings. Further these systems are limited by their power management and lack of adaptability.

SUMMARY OF THE DISCLOSURE

In an aspect, a distributed security system is presented. The system can include a detection unit disposed at a first location of an environment. The detection unit can comprise a particle sensor configured to detect a particle count proximate to the first location of the environment and also a detection unit housing configured to enclose at least a portion of the particle sensor. The system may further include a camera unit disposed at a second location of the environment. The camera unit can comprise a field of vision encompassing the first location and the camera unit configured to capture a video of the first location. Additionally, the system can include a server communicatively connected to the detection unit and the camera and configured to associate the particle count with the video.

In another aspect, a building management system is presented. The system can include a detection unit disposed at a first location of an environment. The detection unit can comprise a particle sensor configured to detect a particle count of a substance proximate to the first location of the environment and a detection unit housing configured to enclose at least a portion of the particle sensor. The system can also include an HVAC system disposed proximate to the first location of the environment. The HVAC system can comprise an air filter configured to filter the substance. Additionally, the system can include a server communicatively connected to the detection unit and the HVAC system and configured to activate the air filter.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIG. 2A is an isometric view illustrating a housing for an aerosolized substance detection system, according to embodiments.

FIG. 2B is an isometric cutaway view illustrating a housing for an aerosolized substance detection system, according to embodiments.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

Figure 1:
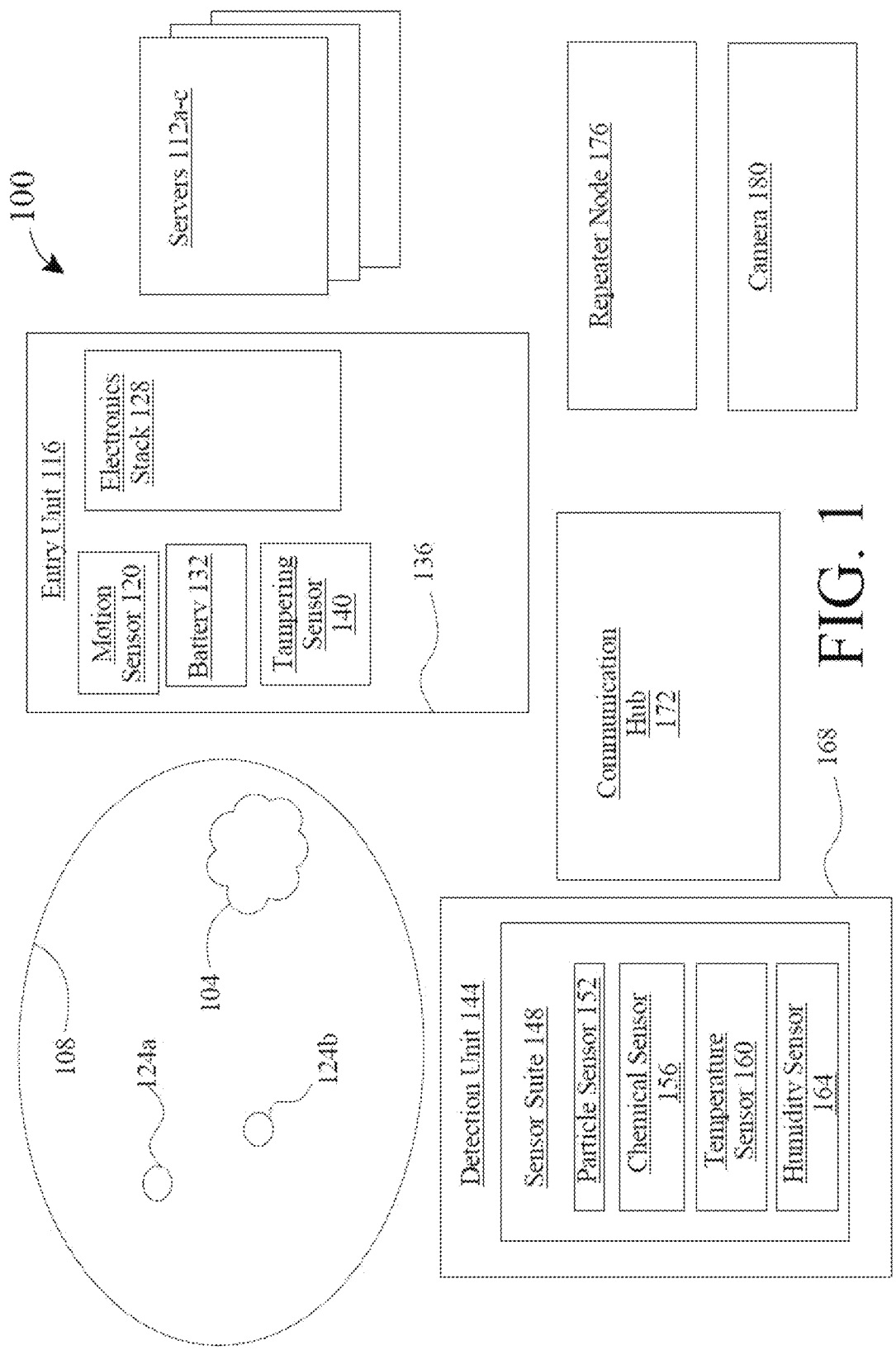
FIG. 1 is a block diagram illustrating an aerosolized substance detection system, according to embodiments.

At a high level, with reference to FIG. 1, a system of sensors and components to detect vaporized substances of interest within an environment is provided. The system comprises an entry device and a detection device disposed at respective, distinct locations in an environment 108 where a substance such as a vaporized aerosol containing chemical particles may be present and wherein the entry device and detection device may each be connected to at least one of a plurality of servers 112*a-c*. In an aspect, each device may include a housing, which may encapsulate at least a portion of each of the entry device and detection device system components. The housing may be disposed in an environment 108 having a vaporized substance of interest present. Substances of interest may be present and have a microscopic or macroscopic size, a distribution, and a count. Devices of the system may enter low power consumption modes to extend component and battery 132 life.

Referring now to FIG. 1, an aerosolized substance detection system is configured to detect substances of interest 104 within environment 108 and generate an alarm based on detected substance and/or particles. Substances of interest (also referred to herein as "substances") 104 may comprise aerosolized particles, disallowed and/or discouraged substances (such as vapor from a vaping device or e-cigarette, smoke from tobacco, smoke from drug use, or the like), gasses, gaseous clouds, gaseous chemicals, biologicals (such as viruses, bacteria, pathogens, or the like) or any combination thereof. Further, aerosolized substance detection system 100 can be configured to transmit and store a signal indicating an alarm and/or data relating to detected substances to at least one server of a plurality of servers 112*a-c*. Any and all signals generated by aerosolized substance detection system 100 may be additionally or alternatively stored onboard in a memory (discussed below) or remotely on servers 112*a-c*.

With continued reference to FIG. 1, aerosolized substance detection system 100 includes an entry unit 116 disposed at a first location within environment 108. Entry unit 116 is configured to generate a detection signal in response to a detected triggering event within environment 108. For detecting a triggering event, entry unit 116 can comprise a trigger sensor such as motion sensor 120, particle sensor (similar or the same as particle sensor 152, discussed below), chemical sensor (similar or the same as chemical sensor 156, discussed below), temperature sensor (similar or the same as temperature sensor 160, discussed below), humidity sensor (similar or the same as particle sensor 164, discussed below), camera (similar or the same as camera 180, discussed below), or a tamper sensor (similar or the same as tamper sensor 140, discussed below). A "triggering event", as used herein, comprises an event of interest that occurs within or proximate to one or more locations within environment 108 such as detected movement, detected predetermined substances of interest, detected particle counts, detected particle densities, detected temperatures, detected objects within a video and/or image, detected humidity, a detected tamper event, or any combination thereof.

For example, entry unit 116 can include a motion sensor 120 configured to detect movement in and/or proximate to its location within an environment 108 and generate a detection signal in response to detected movement in the environment 108. In embodiments, motion sensor 120 includes one or more sensors, each configured to detect motion, proximity, and/or presence within or proximate to the entry unit's location. Motion sensor 120 is configured to detect the motion, proximity, and/or presence of one or more objects 124*a-b* within environment 108. For example, motion sensor 120 may include light sensors (such as infrared sensors, passive infrared sensors, area reflective type sensors, etc.), microwave sensors, ultrasound sensors, vibration sensors, dual technology sensors, or any combination thereof, to name a few. Objects 124*a-b* may include people, animals, vehicles, inanimate objects 124*a-b*, or any combination thereof, to name a few examples. For example, motion sensor 120 can be configured to detect the motion of a person in environment 108. According to embodiments, motion sensor 120 can be configured to detect when objects 124*a-b* enter or leave environment 108 such as by observing the motion, proximity, and/or presence of objects 124*a-b*.

According to embodiments, and still referring to FIG. 1, environment 108 may include an area of interest in which vaporized aerosols are prohibited or discouraged. For example, environment 108 can include areas of a school (such as classrooms, halls, bathrooms, school yards, gymnasiums, school buses, or any combination thereof, to name a few), rental vehicles (such as rental cars, moving trucks, rented recreational vehicles, etc.), business vehicles (such as company cars, vans, tractor-trailer trucks, etc.), rideshare vehicles, areas of an airplane, boat, train, and/or bus (such as cockpits, cabins, bathrooms, or any combination thereof, to name a few), residences, rental homes, rental apartments, retirement communities, hotels (such as hotel rooms, hotel conference rooms, ballrooms, etc.), motel rooms, workplaces (such as offices, restaurants, factories, warehouses, parking structures, or any combination thereof, to name a few), hospitals, rehabilitation facilities, correctional facilities, or any combination thereof.

In embodiments, and with continued reference to FIG. 1, when entry unit 116 detects a triggering event such as motion, proximity, duration, speed, size, detection of predetermined substances of interest, a tampering event, and/or presence of objects 124*a-b* within environment 108, entry unit 116 may be configured to generate a detection signal. A detection signal may include an analog and/or digital signal indicating details of a triggering event such as the location, area, motion, proximity, and/or presence of objects 124*a-b* within a location of environment 108, a particle count at a location within environment 108, detection of a tampering event, or any combination thereof. According to embodiments, entry unit 116 can include a motion sensor 120 configured to generate a detection signal when it detects an object entering, within, or proximate to an entry unit's location within environment 108. In embodiments, a detection signal may indicate a time, size, speed, duration, and/or quantity of objects 124*a-b* entering, within, or proximate to an entry unit's location within environment 108.

According to embodiments, and with further reference to FIG. 1, the sensors (such as motion sensor 120) of entry unit 116 can be electronically and/or communicatively coupled to an entry unit electronics stack 128 and may be configured to provide a detection signal to entry unit electronics stack 128 when the detection signal is generated. In embodiments, entry unit electronics stack 128 may be proximate to motion sensor 120 while in other embodiments entry unit electronics stack 128 may be remote from motion sensor 120. In embodiments, entry unit electronics stack 128 may comprise analog and/or digital circuitry configured to condition, analyze, and/or transform received signals. For example, entry unit electronics stack 128 may comprise a microprocessor, a microcontroller, a power microcontroller, a processor, an analog-to-digital converter, a digital-to-analog converter, logic circuitry, a memory (e.g. flash memory, hard disk drive, solid state memory, random-access memory, programmable read-only memory, electronically erasable programmable read-only memory, or any combination thereof, to name a few), or any combination thereof, to name a few. According to embodiments, entry unit electronics stack 128 may be configured to store received signals from motion sensor 120 in a memory.

In embodiments, and with continued reference to FIG. 1, entry unit electronics stack 128 may be configured to determine a triggering event (such as if an object has entered environment 108, a predetermined substance has been detected, etc.) by analyzing a received detection signal. Analyzing a detection signal may include comparing a level of the detection signal to a predetermined threshold value. For example, analyzing a detection signal may include comparing a level of the detection signal to a movement threshold value, comparing a time indicated by the detection signal to a time threshold, comparing a duration indicated by the detection signal to a duration threshold, comparing a size indicated by the detection signal to a size threshold, or any combination thereof, to name a few. In embodiments, these predetermined thresholds may be stored within entry unit electronics stack 128 while in other embodiments they may be stored remotely. According to embodiments, a user may set, adjust, cancel, or otherwise manipulate these threshold levels from a user device, whether those thresholds are stored within entry unit electronics stack 128 or remotely in servers 112a-c.

According to embodiments, entry unit electronics stack 128 can be configured to send a detection signal to communication hub 172 which may be configured to analyze the received detection signal according to predetermined threshold values stored on communication hub 172. Communication hub 172 may further be configured to transmit a received detection signal to servers 112a-c which may be configured to analyze the received detection signal according to predetermined threshold values stored on servers 112a-c.

In embodiments, and further referring to FIG. 1, entry unit electronics stack 128 may be electronically or communicatively coupled to an energy storage device, such as a battery 132. A battery 132 may comprise one or more battery elements/batteries disposed in one or more locations within environment 108. In embodiments, a respective battery 132 may be proximate to entry unit 116, detection unit 144, communication hub 172, repeater node 176, camera 180, or any combination thereof. A respective battery 132 may include one or more battery 132 elements in parallel and/or series configured to provide power to at least a portion of entry unit 116 (including motion sensor 120, electronics stack 128, and/or tampering sensor 140), detection unit 144 (including sensor suit 148 which may include particle sensor 152, chemical sensor 156, temperature sensor 160, and humidity sensor 164), communication hub 172, repeater node 176, camera 180, or any combination thereof. For example, battery 132 may comprise one or more lithium-ion batteries, alkaline batteries, lead-acid batteries, aluminum-ion batteries, flow batteries, magnesium-ion batteries, metal-air electrochemical cells, nickel-ion batteries, zinc-ion batteries, or any combination thereof, to name a few. According to embodiments, a battery 132 may comprise an alternative power source such as an alternating current ("AC") power source, direct current ("DC") power source, power over ethernet (PoE), a solar photovoltaic cell, wireless power transfer, a wind turbine, or any combination thereof, and/or power electronics such as a half-bridge rectifier, full-bridge rectifier, inverter, maximum-point power tracker, power converter (such as a buck converter, boost converter, buck-boost converter, flyback converter, transformer, etc.), or any combination thereof, to name a few. In embodiments, if a battery 132 includes PoE, a DC power source, and/or an AC wall outlet power, operation of at least a portion of entry unit 116 (including motion sensor 120, electronics stack 128, and/or tampering sensor 140), detection unit 144 (including sensor suit 148 which may include particle sensor 152, chemical sensor 156, temperature sensor 160, and humidity sensor 164), communication hub 172, repeater node 176, camera 180, or any combination thereof connected to such a battery 132 may remained powered at all times. A battery 132 and/or energy storage device may alternatively or additionally include a kinetic, capacitive, inductive, fuel-based (e.g. a fuel cell) and/or any other device or component for storage of electrical energy and/or chemical or other energy for conversion to electronic energy.

According to embodiments, and with continued reference to FIG. 1, a battery 132 and/or energy storage device may be configured to provide power to at least a portion of entry unit 116, detection unit 144, communication hub 172, repeater node 176, camera 180, or any combination thereof based upon an electronics stack. In embodiments, an electronics stack may comprise power management circuitry including, for example, a power microcontroller, switches, relays, transistors, linear regulators, power converters, or any combination thereof, to name a few.

Still referring to FIG. 1, power management circuitry of entry unit electronics stack 128 may be configured to provide power from a battery 132 to at least a portion of sensor suite 148, entry unit electronics stack 128, tampering sensor 140, communication hub 172, repeater node 176, camera 180, or any combination thereof based upon a received detection signal from motion sensor 120, or another sensor configured to act as a trigger for the power management circuitry, and may include a real time clock configured to keep track of time. According to embodiments, entry unit electronics stack 128 may be configured to provide power from battery 132 to at least a portion of sensor suite 148, and/or tampering sensor 140 according to a size, duration, time, and/or quantity of detected objects 124a-b indicated by a detection signal, according to a time the detection signal is received, or any combination thereof. For example, when a detection signal indicates that an object has entered environment 108, entry unit electronics stack 128 may be configured to provide power to a detection unit 144 as described below, such that detection unit 144 is adequately powered to take measurements.

According to embodiments, providing power from a battery 132 to at least a portion of sensor suite 148, entry unit electronics stack 128, tampering sensor 140, communication hub 172, repeater node 176, camera 180, or any combination thereof may include generating a wake-up signal. For example, a wake-up signal may be generated when movement is detected by movement sensor 120. A wake-up signal may comprise an analog or digital signal configured to switch at least a portion of sensor suite 148, entry unit electronics stack 128, tampering sensor 140, communication hub 172, repeater node 176, camera 180 from a sleep, low-power mode, and/or standby mode to an active or armed mode.

In embodiments, and continuing to refer to FIG. 1, entry unit electronics stack 128 may be configured to monitor a power and/or battery 132 level of battery 132 and generate a signal including data representing the current power and/or battery 132 level of battery 132. Data representing a current power and/or battery 132 level of battery 132 may represent current, historical, or projected power and/or battery 132 level of battery 132 and may be expressed as a percentage, a value (such as in amp hours), graphically, or any combination thereof. According to embodiments, entry unit electronics stack 128 may be configured to compare data representing a current power and/or battery level of battery 132 to a predetermined low-battery threshold which may be stored in entry unit electronics stack 128 or servers 112a-c. In embodiments, entry unit electronics stack 128 may be configured to generate a low-battery alert when a current power and/or battery level of battery 132 is equal to or less than a low-battery threshold value. A low-battery alert may include a signal including representing that battery 132 is at low power and may be configured to be displayed on a display or user device. In embodiments, a low-battery alert may include a signal configured to induce a change in the color of a display such as an LED. For example, a low-battery alert may be configured to switch an LED from green to red.

According to embodiments, and still referring to FIG. 1, entry unit electronics stack 128 may be configured to provide and/or transmit a signal including data representing current power and/or battery level of battery 132 to other devices and/or units in vaporized aerosol detection system 100, and/or to one or more servers 112*a-c*; such devices, units, and/or servers 112*a-c* may be configured to compare data representing current power and/or battery level of battery 132 to a predetermined low-battery threshold. In embodiments, devices, units, and/or servers 112*a-c* may be configured to generate a low-battery alert when a current power and/or battery level of battery 132 is equal to or less than a low-battery threshold value. According to embodiments, a user may set, adjust, cancel, or otherwise manipulate a low-battery threshold level from a user device, whether the low-battery threshold is stored within entry unit electronics stack 128 or remotely in additional devices, units, and/or servers 112*a-c*.

According to embodiments, and with further reference to FIG. 1, entry unit electronics stack 128 may include equipment configured to receive signals generated from any disclosed or undisclosed sensor present within vaporized aerosol detection system 100. Entry unit electronics stack 128 may include analog and/or digital circuitry configured to condition, analyze, and/or transform received signals. For example, entry unit electronics stack 128 may include a microprocessor, a microcontroller, a power microcontroller, a processor, an analog-to-digital converter, a digital-to-analog converter, logic circuitry, or any combination thereof, to name a few.

According to embodiments, and still referring to FIG. 1, entry unit electronics stack 128 may include equipment necessary for wireless transmission of electronic signals to other devices, units, and/or servers 112*a-c*. For example, entry unit electronics stack 128 may comprise a transceiver and can be configured to be communicatively coupled to a server by a cellular phone network(s), wireless local area network (WLAN), wireless personal area networks (WPAN), wireless wide area networks (WWAN), wireless sensor networks, satellite communication networks, terrestrial microwave networks, Bluetooth, WiFi, ZigBee, low-power long range wide area network (LoRaWan and LoRa), internet, ethernet, a wireless ad-hoc network also known as a wireless mesh network, and/or any combination thereof. In embodiments, these predetermined threshold values may be stored within servers 112*a-c*.

Further referring to FIG. 1, each of one or more servers 112*a-c* may include any computing device as described in this disclosure, including without limitation a microcontroller, microprocessor, digital signal processor (DSP) and/or system on a chip (SoC) as described in this disclosure. Each of one or more servers 112*a-c* may include, be included in, and/or communicate with a user device such as a mobile telephone or smartphone. Any server of one or more servers 112*a-c* may include a single computing device operating independently, or may include two or more computing devices operating in concert, in parallel, sequentially or the like; two or more computing devices may be included together in a single computing device or in two or more computing devices. Any server of one or more servers 112*a-c* may interface or communicate with one or more additional devices as described below in further detail via a network interface device. Network interface devices may be utilized for connecting a server to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Any server of one or more servers 112*a-c* may include but is not limited to, for example, a computing device or cluster of computing devices in a first location and a second computing device or cluster of computing devices in a second location. Any server of one or more servers 112*a-c* may include one or more computing devices dedicated to data storage, security, distribution of traffic for load balancing, and the like. Any server of one or more servers 112*a-c* may distribute one or more computing tasks as described below across a plurality of computing devices, which may operate in parallel, in series, redundantly, or in any other manner used for distribution of tasks or memory between computing devices. Any server of one or more servers 112*a-c* may be implemented using a "shared nothing" architecture in which data is cached at the worker, in an embodiment, this may enable scalability of system 100 and/or computing device.

Still referring to FIG. 1, any device, unit, and/or server described in this disclosure may be designed and/or configured to perform any method, method step, or sequence of method steps in any embodiment described in this disclosure, in any order and with any degree of repetition. For instance, any device, unit, and/or server may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Any device may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, entry unit 116 includes an entry unit housing 136 configured to enclose at least a portion of the trigger sensor, such as motion sensor 120. A housing may have a shape having a number of sides or faces which each side comprising opposite, opposing surfaces with a thickness between them. According to embodiments, a first surface of a side may form a portion of an outer wall of housing and a second, opposing and opposite surface of the side can form a portion of an inner wall of housing. For example, a housing may include a hollow three-dimensional prism with an outer mold line with a thickness. In embodiments, a housing may be one continuous shape or may be mechanically fastened smaller individual pieces configured to encase or enclose at least a portion of motion sensor 120, a tampering sensor 140, entry unit electronics stack 128, battery 132, or any combination thereof.

According to embodiments, and with further reference to FIG. 1, a housing may be configured to snap together non-permanently such that housing may be pulled apart by a user for allowed access to interior components. A housing may comprise injection molded plastics like high-density polyethylene (HDPE) or Acrylonitrile butadiene styrene (ABS), stamped or otherwise machined metal like aluminum, steel alloys, tin, or other alloys. A housing may comprise a back plate which can be permanently or temporarily mechanically fastened to a cover through screws, nails, snap connectors, epoxy, glue, double-sided tape, rivets, or another undisclosed method alone or in combination. In embodiments, a housing may, in a hollow space within, enclose or encase at least a portion of motion sensor 120, sensor suite 148 (including particle sensor 152, chemical sensor 156, temperature sensor 160, humidity sensor 164, or any combination thereof), alarm, battery 132, entry unit electronics stack 128, tampering sensor 140 or a portion of any which may allow its optimal operation.

In an embodiment, and continuing to refer to FIG. 1, entry unit 116 may also include a tampering sensor 140. Tampering sensor 140 may include one or more sensors disposed within or on housing and may be configured to detect a tampering event. A tampering event may include someone breaking open entry unit 116, someone moving entry unit 116, someone touching entry unit 116, someone hitting entry unit 116, someone shaking entry unit 116, someone disconnecting entry unit 116, or any combination thereof. According to embodiments, tampering sensor 140 may be configured to detect a tampering event by detecting that an object is in close proximity to entry unit 116, movement of entry unit 116, integrity of housing, or any combination thereof. For example, tampering sensor 140 may comprise one or more sensors configured to detect a tampering event when a person is attempting to move or break open entry unit 116.

According to embodiments, and still referring to FIG. 1, tampering sensor 140 may be configured to generate a tamper alarm when a tampering event is detected. A tamper alarm may include an electronic signal configured to induce an audible alert, a visual alert, a tactile alert, and/or any alert sufficient to alert that a tamper event occurred from the alarm. In other embodiments, tampering sensor 140 may generate signals including data representing that an object is in close proximity to entry unit 116, movement of entry unit 116, integrity of housing, or any combination thereof. Tampering sensor 140 may be electronically and/or communicatively coupled to entry unit electronics stack 128 and configured to provide said signals to entry unit electronics stack 128. In embodiments, entry unit electronics stack 128 may be configured to detect that a tampering event has occurred based upon received signals including data representing that an object is in close proximity to entry unit 116, movement of entry unit 116, integrity of housing, or any combination thereof. Entry unit electronics stack 128 may be configured to generate a tamper alarm when a tampering event has occurred. A user may enable, disable, or otherwise manipulate the tamper alarm from a user device and/or server. Tamper alarm may also be disabled through, for example, an interlock such as a magnetic switch disposed in or on housing, which may be engaged, for example, by a magnetic key fob held by a potential maintainer or user. Tamper alarm may include and/or trigger an audible alarm, which may include any audio output device such as without limitation speakers or the like. An audible alarm may provide a local alarm to warn occupants and nearby staff that tampering has been detected. An alarm may include an auditory alarm or signaling device (such as a buzzer, siren, horn, etc.), a visual alarm or signaling device (such as an LED, strobe light, laser, LED screen, LCD screen, etc.), tactile alarm or signalizing device (such as a vibration alarm, motor, etc.), or any combination thereof. Activating an alarm may include sending an electronic signal to the alarm to induce an audible alert (such as, for example, a chime, chirp, siren, beep, or otherwise artificial noise), a visual alert (such as, for example, flashing lights, a display, a strobe, color lights, etc.), a tactile alert (such as vibration, shaking, etc.), and/or any alert sufficient to alert that a detection event has occurred in environment 108. A user may adjust alarm volume, alarm sound, alarm light display, and disable alarm through user device and/or server.

With continued reference to FIG. 1, entry unit 116 may have a polling mode. In the polling mode, entry unit 116 may be configured to periodically perform a polling cycle which can include powering on for a predetermined amount of time, checking for a triggering event such as motion, predetermined detection of a substance, a tampering event, etc., and powering off/entering a sleep or standby mode. In embodiments, the predetermined amount of time an entry unit is powered on during a polling cycle can include seconds, minutes, hours, days, weeks, or any combination thereof. According to embodiments, a polling cycle can be performed periodically at predetermined intervals which can include a predetermined amount of time such as seconds, minutes, hours, days, days of the week, dates, weeks, or any combination thereof. In embodiments, a polling cycle may further comprise transmitting any detected triggering, detection, or tampering events to servers 112a-c. According to embodiments, a polling cycle can comprise evaluating a communicative connection between entry unit 116 and one or elements of aerosolized substance detection system 100 (such as, for example, detection unit 144, communication hub 172, repeater node 176, and/or servers 112a-c). Evaluating a communicative connection can comprise evaluating a number of packets sent from and received by entry unit 116, locating IP addresses, receiving/transmitting authentication signals, or any combination thereof. In embodiments, entry unit 116 can determine that a communicative connection between entry unit 116 and one or elements of aerosolized substance detection system 100 has failed, such as, for example, when entry unit 116 is offline or a local network has gone down. When entry unit 116 has determined that a communicative connection has failed, entry unit 116 may be configured to determine a failed detection signal. The failed detection signal can comprise a signal configured to indicate that entry unit 116 is offline and can include an alert, switching the color of an LED, inducing an audible alarm, or any combination thereof—to name a few. In embodiments, entry unit 116 may be configured to transmit data to communication hub 172 and/or servers 112a-c during a polling cycle such as data representing detected triggering events, battery levels, device health, diagnostic information, or any combination thereof. According to embodiments, entry unit 116 may be configured to receive data from communication hub 172 and/or servers 112a-c during a polling cycle such as alerts, firmware updates, software updates, threshold values, or any combination thereof.

According to embodiments, polling cycles for entry unit 116 can be determined by a watchdog timer. A watchdog timer can comprise hardware and/or software and a power source configured to perform a polling cycle at predetermined intervals of time (such as every 12 or 14 hours) and dictate the predetermined length or time of the polling cycles (such as for 1-2 hours). In embodiments, a watchdog timer may operate a duty cycle in which entry unit 116 is powered off, except for the watchdog timer, for some proportion of a period, and powers on briefly to check for motion; duty cycle may, for instance, switch on entry unit 116 and/or motion sensor 120 for 200 ms every second or the like. In embodiments, polling cycles for entry unit 116 can be determined by a clock timer. A clock timer can comprise software and/or hardware such as a processor, microprocessor, microcontroller, quartz crystal, power source, and/or memory and can be configured to perform a polling cycle at predetermined, variable intervals of time (such as every 4 or 10 hours) and dictate the predetermined, variable length or time of the polling cycles (such as for 1-2 hours). In embodiments, the predetermined, variable intervals of time and length or time can be varied or set by servers 112a-c or a user device.

Entry unit 116 may have a scanning mode, in which the entry unit 116 is configured to communicate with a detection unit 144. Entry unit 116 may be configured to enter the scanning mode when a triggering event is detected such as when the motion sensor 120 detects motion; entry unit 116 may remain in scanning mode until a cessation of the triggering event such as when motion is detected and/or until a scan for particles as described below has completed. A timer such as a watchdog timer or the like may count down from initiation of scanning mode, a latest detected motion, or the like, where count-down to zero may cause transition into polling mode, and count-down may be reset upon detection of motion, particles, or the like. Transitions between modes may be governed by a processor, finite state machine, or the like.

According to embodiments any element of aerosolized substance detection system 100 (such as detection unit 144, communication hub 172, camera 180, etc.) may have a polling mode similar or the same as entry unit 116.

Still referring to FIG. 1, aerosolized substance detection system 100 includes a detection unit 144 communicatively connected to the entry unit 116. As used herein, "communicative connecting" is a process whereby one device, component, or circuit is able to receive data from and/or transmit data to another device, component, or circuit. In an embodiment, communicative connecting includes electrically coupling at least an output of one device, component, or circuit to at least an input of another device, component, or circuit. Communicative connection may be wired, wireless, effected using magnetic and/or optical couplings, or the like; communicative connection may be performed according to any process and/or protocol for communication between devices and/or units as described in this disclosure. Detection unit 144 may include a particle sensor 152 configured to detect a particle count of the environment 108 in response to the generation of the detection signal. In embodiments, detection unit 144 is disposed a different location from entry unit 116 within environment 108.

In embodiments, and with further reference to FIG. 1, detection unit 144 may include a sensor suite 148. When power is provided to sensor suite 148 from a battery 132, sensor suite 148 may be configured to detect substances 104 in or proximate to detection unit's 144 location within environment 108. Substances 104 may include one or more substances 104, gases, and/or particles that have been aerosolized in at least a portion of environment 108. For example, substances 104 may include chemical particles from a nicotine vaping device, a cannabinoid vaping device, a tetrahydrocannabinol vaping device, a chemical spill (such as dimethyl sulfate, toluene diisocyanate), hazardous gas clouds (such as arsine, dimethyl sulfate, toluene, hydrogen azide, hydrogen cyanide, nitrogen dioxide), animal excrement (such as ammonia), tobacco smoke, carbon dioxide, carbon monoxide, methamphetamine, fentanyl, anhydrous ammonia, or any combination thereof, to name a few. Sensor suite 148 may be configured to detect a quantity (i.e. particle count), density, size, structure, and/or dispersion of substances 104 and may include a particle sensor 152, a chemical sensor 156, a temperature sensor 160, a humidity sensor 164, or any combination thereof. In embodiments, sensor suite 148 may be electronically and/or communicatively coupled to a detection unit 144 electronics stack, which may be implemented in any manner suitable for entry unit electronics stack as described above. Communicative coupling may comprise a connection sufficient to transfer data back and forth between sensor suite 148 and detection unit 144 electronics stack. Communicative coupling may be a wired or wireless connection that may employ electronic buses, ethernet, internet, WiFi, Bluetooth, cellular network, or another undisclosed method alone or in combination. Additionally, or alternatively, detection unit 144 and/or sensor suite 148 may be communicatively coupled to at least a server. This communicative coupling, as disclosed, is a connection sufficient for transferring data between sensor suite 148 and at least a server and can include WiFi, ethernet, cellular networks, Bluetooth, NB-IoT, LTE CAT1, LTE-M1, CAT NB1, long-range (LoRa) communication connects, or any combination thereof, to name a few. In embodiments, sensor suite 148 can include a GPS unit configured to determine the location, coordinates, room, and/or area of a detection unit 144 within environment 108.

In an embodiment, and still referring to FIG. 1, sensor suite 148 may include particle sensor 152. Particle sensor 152 may include one or more sensors that are configured to detect a quantity (i.e. particle count), size, structure, dispersion, or any combination thereof, of substances 104. In embodiments, particle sensor 152 may be configured to differentiate ambient particles present in environment 108 to substances 104 of interest that may trigger an alert within the system. For example, particle sensor 152 may be configured to compare a historical reading of particles in environment 108 to a detection of substances 104 to determine what particles within substances 104 are ambient in environment 108 and which particles may be substances 104 of interest. According to embodiments, particle sensor 152 may be configured to measure or otherwise detect the quantity (i.e. particle count), size, structure, dispersion, or any combination thereof, of particles present in substances 104 and may be configured to translate those readings into electronic signals. According to embodiments, particle sensor 152 may be electronically and/or communicatively coupled to detection unit 144 electronics stack and may be configured to send signals including data representing the quantity (i.e. particle count), size, structure, dispersion, or any combination thereof, of particles present in substances 104 to detection unit 144 electronics stack.

In embodiments, and with continued reference to FIG. 1, sensor suite 148 may include chemical sensor 156. Chemical sensor 156 may include one or more sensors configured to detect a structure, size, shape, and/or composition of particles in order to determine chemical composition of substances 104 in environment 108. Chemical sensor 156 may include a printed electrochemical sensor 156, Complementary Metal Oxide Semiconductor (CMOS) circuit, metal oxide, nanotube, micro cantilever, micro hot plates, mobility spectrometer (ion or differential), mass spectrometer, infrared spectrometer, or any combination thereof, to name a few examples. In embodiments, chemical sensor 156 may be configured to differentiate ambient chemicals present in environment 108 to chemicals of interest that may trigger an alert within the system. For example, chemical sensor 156 may be configured to detect a plurality of chemicals and/or gaseous or aerosolized particles, some of which may include nicotine, cannabinoids, tetrahydrocannabinoids, particles from a chemical spill (such as dimethyl sulfate, toluene diisocyanate), particles in hazardous gas clouds (such as arsine, hydrogen azide, hydrogen cyanide, nitrogen dioxide), particles from animal excrement (such as ammonia), tobacco smoke, carbon dioxide, carbon monoxide, sulfur dioxide, ozone, nitrogen dioxide, respiratory irritants, indicators of indoor air quality, or any combination thereof. Chemical sensor 156 may translate readings it collects to an electronic signal including data representing the structure, size, shape, and/or composition of particles. In embodiments, chemical sensor 156 may be electronically and/or communicatively connected and/or coupled to detection unit 144 electronics stack and may be configured to send the signals including data representing the structure, size, shape, and/or composition of particles to detection unit 144 electronics stack.

According to embodiments, and still referring to FIG. 1, sensor suite 148 may include temperature sensor 160. Temperature sensor 160 may include one or more sensors configured to determine a temperature of environment 108. Temperature, for the purposes of this disclosure, is an amount of heat energy present in environment 108. One of ordinary skill in the art would appreciate that temperature is truly the amount of kinetic energy present in an environment 108 on the atomic level, and for the purposes of this disclosure, temperature as it affects electronics, humans, objects 124*a-b*, and/or gaseous elements may be measured in Fahrenheit, Celsius, Kelvin and/or the like. According to embodiments, temperature sensor 160 may determine a temperature of environment 108 to help assess the dispersion, density, and/or composition of substances 104 in environment 108. Additionally, temperature sensor 160 may determine the temperature of environment 108 to assess the health of electronics and sensors present within vaporized aerosol detection system 100. In embodiments, temperature sensor 160 may be configured to generate a signal including data representing a detected temperature of environment 108 and provide this signal to detection unit 144 electronics stack, at least a first server, any other device and/or unit in system 100, or any combination thereof. In embodiments, this signal may also include data alerting a user of a change in temperature of environment 108 over or under certain thresholds or to alert a user of aerosolized particles evidenced by a change in temperature. According to embodiments, temperature sensor 160 may translate readings it collects into electronic signals including data representing the detected temperatures. Temperature sensor 160 may be electronically and/or communicatively connected and/or coupled to detection unit 144 electronics stack and may be configured to provide such signals to detection unit 144 electronics stack.

In embodiments, and further referring to FIG. 1, sensor suite 148 may include humidity sensor 164. Humidity sensor 164 may include one or more sensors configured to determine an amount of humidity present in environment 108. Humidity, for the purposes of this disclosure, is a quantity of vaporized water in a gaseous area, in this case air of environment 108. Humidity sensor 164 may be further configured to measure humidity in one of three general methods: absolute, relative, and specific. Absolute humidity describes the water content of air and is expressed in either grams per cubic meter or grams per kilogram. Relative humidity may be expressed as a percentage and indicate a present state of absolute humidity relative to a maximum humidity given the same temperature (as determined by temperature sensor 160). Specific humidity is the ratio of water vapor mass to total moist air parcel mass. Humidity sensor 164 may be configured to determine humidity of environment 108 in order to detect a change in air density, which may be due to the presence of substances 104. Humidity sensor 164 may additionally or alternatively be configured to determine humidity of environment 108 in order to ascertain the optimal range of humidity for the complement of other sensors present in sensor suite 148, in an embodiment. Humidity sensor 164 may translate readings it collects into electronic signals including data representing the humidity in environment 108. In embodiments, humidity sensor 164 may be electronically and/or communicatively connected and/or coupled to detection unit 144 electronics stack and may be configured to provide such signals to detection unit 144 electronics stack.

Continuing to refer to FIG. 1, detection unit 144 may include a detection unit housing 168 configured to enclose at least a portion of the particle sensor 152. Detection unit housing 168 may be implemented in any manner suitable for entry unit housing 136. Detection unit housing 168 may include cut-throughs and openings where a sensor may need access to an air sample of environment 108 or where a vaporized aerosol may enter housing to reach any internal component. Detection unit 144 may include a tampering sensor, which may include any component suitable for use as entry unit 116 tampering sensor 140 above, including without limitation a piezo-electric vibration sensor used to measure unexpected vibrations in the device related to device tampering, a conductivity sensor triggered where conductivity is altered by alterations to housing, and/or an accelerometer or the like for detection of movement of housing and/or components thereof. In some embodiments, detection unit housing 168 housing can be configured to be handheld and/or portable while in other embodiments detection unit housing 168 can be configured to be stationary, such as when affixed/coupled to a surface.

Further referring to FIG. 1, at least one of entry unit housing 136 and detection unit housing 168 may include venting openings. Detection unit housing 168 may be configured to be disposed inline in an air circulation system such as without limitation a duct, vent, or the like. Aerosolized substance detection system 100 may include an alarm configured to produce an alert in response to the detected particle count; alarm may be in a self-contained unit, which may include any elements and/or components of a unit as described in this disclosure, or may be incorporated in and/or communicatively connected to any unit as described in this disclosure, including without limitation entry unit 116, detection unit 144, communication hub 172, a mobile device, and/or a repeater. Aerosolized substance detection system 100 temperature sensor 160, which may be configured to detect a temperature of environment 108 in response to generation of a detection signal.

Still referring to FIG. 1, detection unit 144 may include any battery 132, energy storage device, and/or energy source suitable for use with entry unit 116. Detection unit 144 may include an audible alarm, which may include any alarm suitable for use with entry unit 116; audible alarm may provide local alarm to warn occupants and nearby staff that a detection event or tampering was detected. Detection unit 144 electronics stack may also be configured to calibrate and/or trim any and all sensors that may be present within aerosolized substance detection system 100 and/or coupled to the system remotely. Calibration of sensors and systems may comprise zeroing a sensor after a reading, power cycle, malfunction, or the like.

Further referring to FIG. 1, detection unit 144 may be configured to detect a detection event as a function of the particle count. Detection unit 144 may be configured to detect the detection event as a function of comparing the particle count to a predetermined threshold. As a non-limiting example, in embodiments, detection unit 144 electronics stack may be configured to determine if substances of interest 104 are present. Substances of interest 104 may include any particles that may be a cause of concern for environment 108. For example, substances of interest 104 may include substances that are disallowed in environment 108 (such as nicotine, cannabinoids, tetrahydrocannabinoids, tobacco smoke, etc.), substances that are hazardous (carbon monoxide, carbon dioxide, arsine, hydrogen azide, hydrogen cyanide, nitrogen dioxide, viruses, bacteria, pathogens, etc.), undesirable substances for environment 108 (tobacco smoke, nicotine, cannabinoids, tetrahydrocannabinoids, ammonia from pet excrement, dust, pollen, mold, etc.), or any combination thereof, to name a few. According to embodiments, determining whether substances of interest 104 are present in environment 108 may include comparing levels of signals received from sensor suite 148 to various, predetermined threshold values. For example, detection unit 144 electronics stack may be configured to receive a signal including data representing a detected structure, size, shape, and/or composition of substances 104 and compare one or more levels included in this signal to predetermined threshold values in order to determine what chemicals (i.e. types of particles) are present in substances 104. According to embodiments, a user may set, adjust, cancel, or otherwise manipulate threshold levels from a user device, whether those thresholds are stored within detection unit 144 electronics stack or remotely in servers 112a-c.

According to embodiments, and still referring to FIG. 1, predetermined threshold values may include a level or measure of a detected structure, size, shape, and/or composition of substances 104. According to embodiments, these predetermined threshold values may be stored in a memory such as a memory of detection unit 144 electronics stack.

In embodiments, and continuing to refer to FIG. 1, detection unit 144 electronics stack and/or servers 112a-c may be configured to determine if a detection event has occurred within or proximate to detection unit's 144 location within environment 108. A detection event, for the purposes of this disclosure is the detection of substances 104, particles, or chemicals of interest in substances 104 within environment 108. For example, a detection event may indicate that a nicotine vaporizer device has been used in environment 108, a chemical spill has occurred in environment 108, smoke is present in environment 108, animal excrement is present in environment 108, or any combination thereof, to name a few examples. According to embodiments, a detection event may further indicate that a quantity, particle density, and/or dispersion of substances 104 of interest within environment 108 have exceeded a predetermined threshold. For example, a detection event may indicate that the particle density of aerosolized vape has exceeded a threshold value in environment 108.

In embodiments, these predetermined threshold values may include a level or measure of a particle density, dispersion, and/or composition of particles that are disallowed, hazardous, or otherwise undesired in environment 108. According to embodiments, these predetermined threshold values can be stored in a memory such as a memory of detection unit 144 or in a respective electronics stack.

According to embodiments, detection unit 144 electronics stack may be configured to trigger an alert based on a detection event by detection unit 144 electronics stack or servers 112a-c. In embodiments, when detection unit 144 electronics stack and/or servers 112a-c have detected that a detection event has occurred, detection unit 144 electronics stack may then generate an alert signal and/or provide power to alarm from battery 132. The alert signal may comprise an electrical signal configured to activate the alarm. In embodiments, the alert can comprise data representing measurements taken during the detection event and may be transmitted to communication hub 172 and/or servers 112a-c.

Still referring to FIG. 1, detection unit 144 may have a low-power mode. When in low-power mode, detection unit 144 may be configured to periodically power on, check for communication from entry unit 116, and power off. Low power mode may operate at a duty cycle or clock timer, governed by a timer such as a watchdog timer; this may be implemented in any manner suitable for implementation of polling mode for entry unit 116. During a duty cycle of a low-power mode, a detection device may check for a signal transmitted from entry unit 116; that is, detection device may check whether entry unit 116 has entered scanning mode as described above. Detection unit 144 may have a detection mode, in which the detection unit 144 is configured to detect a particle count using particle sensor 152. Detection unit 144 may be configured to enter detection mode upon receiving a communication from entry unit 116.

Still referring to FIG. 1, aerosolized substance detection system 100 may include a communication hub 172 communicatively connected, as defined above, to entry unit 116 and detection unit 144, wherein the communication hub 172 is communicatively connected to at least a server. Communicative connection to one device may be affected via another device; in other words, connection to any one device may function as a connection to all devices in system 100. Communication hub 172 may include an electronics stack, which may include any components suitable for use in entry unit electronics stack 128. Communication hub 172 may include a housing, which may include any housing suitable for use as entry unit housing 136. Communication hub 172 may include a tampering sensor 140, which may include any device suitable for use as an entry unit 116 tampering sensor 140 and/or detection unit 144 tampering sensor 140.

With continued reference to FIG. 1, communication hub 172 may be configured to detect a detection event as a function of a particle count; detection may be implemented, without limitation, according to any process described above for detection of detection events. For instance, and without limitation, communication hub 172 may be further configured to detect a detection event as a function of comparing a particle count to a predetermined threshold, for instance as described above. At least a server may be configured to detect a detection event as a function of a particle count; detection may be implemented, without limitation, according to any process described above for detection of detection events. For instance, and without limitation, at least a server may be configured to detect a detection event as a function of comparing a particle count to a predetermined threshold, for instance as described above. Communication hub 172 may be a separate unit from other units in vaporized aerosol detection system 100; alternatively or additionally, any unit of an aerosolized substance detection system 100 described in this disclosure may function as communication hub 172; for instance, communication hub 172 may be, include, and/or be included in at least one of entry unit 116 and detector unit. In an embodiment, operations that require more power, such as communication to a cloud and/or at least a server, may be relegated to the communication hub 172, which may be powered directly via Power over Ethernet (PoE), AC power, or the like.

In embodiments, and further referring to FIG. 1, processing of signals to determine detection events may be additionally or alternatively handled by remotely located servers 112a-c. According to embodiments, servers 112a-c may be configured to determine what particles are present in environment 108 and whether a detection event has occurred by comparing levels of signals received from a respective electronics stack to various, predetermined threshold values. For example, servers 112a-c may be configured to receive a signal including data representing a detected structure, size, shape, and/or composition of substances 104 and compare one or more levels included in this signal to predetermined threshold values in order to determine what chemicals (i.e. types of particles) are present in substances 104.

Still referring to FIG. 1, an aerosolized substance detection system 100 may include a repeater node 176. Repeater node 176 may include any signal reception and/or transmission elements suitable for use with communication hub 172, entry unit 116, and/or detection unit 144, incorporated in and/or connected to any electronics stack suitable for such units and/or elements; for instance, an electronics stack of repeater node 176 may provide Bluetooth, cellular, and/or WiFi communication to and from the other nodes and/or units and/or the communication hub Repeater node 176 may be battery operated, wired, and/or powered via Power over Ethernet depending on configuration of application environment 108. Repeater node 176 may include a housing, which may be implemented in any way described above for a housing of an entry unit 116. Repeater node 176 may include a tampering sensor 140 to warn monitoring personnel if the device is disturbed; tampering sample may be implemented as described above for a tampering sensor 140 of entry unit 116. Repeater node 176 may be configured to receive a signal from at least one of the entry unit 116 and the detection unit 144 and transmit the signal to communication hub 172.

With continued reference to FIG. 1, aerosolized substance detection system 100 may include at least a camera 180 communicatively connected to the entry unit 116 and the detection unit 144. For instance, and without limitation, data captured using sensor suite 148 and/or other components may be combined with video or still camera 180 to provide photographs of occupants exiting an area after an alert occurs or entering an area before an alert occurs. Alert metadata may be used as input to a video/photo analysis package to select corresponding video footage or photos from a camera 180 storage system in a cloud or on communication hub 172 and/or a local server. If video is stored, footage may be converted to still photos. Video and/or still photos may be cropped to focus on faces of occupants; camera 180 information may be transmitted to an application on an electronic device. Alternatively, analyzed camera 180 footage stored on a local server may be transmitted to an application on an electronic device. Transmission may be performed in the form of a text or email, and/or may be transmitted to a software application located on an electronic device. Alternatively, facial photos/video footage may be categorized via facial recognition software analysis to identify occupants from an area by comparing camera 180 information to organizational identification databases. Alternatively, occupant faces may be tagged anonymously and/or sorted according to frequency of appearance. Processed footage transmission may be delayed or real-time.

According to embodiments, and still referring to FIG. 1, camera 180 may be communicatively connected to a respective electronics stack and/or servers 112a-c. Camera 180 may include, for example, video camera 180, still camera 180, SLR camera 180, DSLR camera 180, closed circuit networks, or any combination thereof, to name a few. Camera 180 may be incorporated in and/or attached to an electronics stack of any element and/or unit of vaporized aerosol detection system 100. In embodiments, an electronics stack connected to at least a camera 180 may be configured to provide power from a battery 132 to a camera 180 when a detection event is detected. In response to being provided power and/or when a detection event is detected, a camera 180 may be configured to capture one or more images of environment 108, such as photographs and/or video footage of environment 108. In embodiments, camera 180 may be part of an external system to aerosolized detection system 100.

In embodiments, and with further reference to FIG. 1, captured videos and/or photographs (i.e. images) may be provided to a respective electronics stack and/or servers 112a-c. According to embodiments, units and/or servers 112a-c may each, or in combination, be configured to analyze, process, and compress the captured video and/or photographs. For example, a respective electronics stack and/or servers 112a-c can include facial recognition software configured to identify persons present in the captured videos and/or photographs. Further, a respective electronics stack and/or servers 112a-c can be communicatively coupled with an organizational identification database for the purposes of facial recognition. In embodiments, analyzing the captured video and/or photographs may occur in real-time or may be delayed.

With reference to FIG. 2A, an isometric view of a detection unit 200 as described above, is illustrated, according to embodiments. Detection unit 200 may include motion sensor 216, sensor suite 240 (including particle sensor 220, chemical sensor 224, temperature sensor (not shown for clarity), humidity sensor (not shown for clarity), or any combination thereof), alarm 232, battery 228, electronics stack 236, tampering sensor (not shown for clarity), similar or the same as components hereinbefore described with reference to FIG. 1.

In embodiments, and still referring to FIG. 2, device housing 204, similar or the same as detection unit housing 168, may be configured to enclose at least a portion of motion sensor 216, sensor suite 240 (including particle sensor 220, chemical sensor 224, temperature sensor (not shown for clarity), humidity sensor (not shown for clarity), or any combination thereof), alarm 232, battery 228, electronics stack 236, tampering sensor, and has a shape with at least one set of opposite, opposing surfaces. The shape of housing 204 may include any three-dimensional shape having one or more faces. In embodiments, the shape of housing 204 may be hollow, allowing housing 204 to enclose at least a portion of motion sensor 216, sensor suite 240 (including particle sensor 220, chemical sensor 224, temperature sensor, humidity sensor, or any combination thereof), alarm 232, battery 228, electronics stack 236, and/or tampering sensor. For example, in the illustrated embodiment of FIGS. 2A and 2B, housing 204 may have a shape of a rectangular prism or a hollow box. According to embodiments, each face of the shape of housing 204 forms a respective wall of housing 204. A wall may include a piece of material having opposite, opposing surfaces (e.g. an inner surface and an outer surface) with a thickness between them.

According to embodiments, and further referring to FIG. 2, a wall of housing 204 may include venting 208 which may allow for air to travel within housing 204. Venting 208 may be accomplished by any number or combination of methods including, but not limited to slotting, screens, perforations, cutouts, pass throughs, milled holes, or injection-molded openings, to name a few. By allowing air to travel within housing 204, vaporized aerosol containing chemical particles may be provided to the sensors enclosed with housing 204 for sampling. Venting 208 may be disposed on any or all walls of housing 204 to allow for directed airflow.

In embodiments, and still referring to FIG. 2, housing may be configured to enclose or encase one or more fans. Each fan may be disposed within housing such that the fan is configured to draw air into venting 208 and/or push air out of venting 208. In embodiments, fans enclosed within housing may be configured to create a positive or negative pressure within housing such that air is pulled into and/or forced out of venting 208. According to embodiments, creating a negative or positive pressure within device housing may allow for air to travel within housing so that it may be sampled by the sensors enclosed within housing 204. In embodiments, power may be provided to the fans from battery 132.

According to embodiments, and continuing to refer to FIG. 2, housing 204 may comprise a flapper that allows air to pass through venting 208 such as during sampling but does not allow high pressure bursts of air to enter the system. In other words, flapper may be configured to allow a low flow sampling (such as, for example $<1$ m/s airflow) while preventing higher flow rates or bursts (such as, for example, $>1$ m/s airflow). A flapper may be disposed near venting 208 and configured so that a sudden burst of air may force the flapper closed over at least a portion of venting 208 in order to protect the components enclosed within housing 204 from damage. A flapper may be made of mylar, aluminum, various plastics, or another undisclosed combination of lightweight materials. A closure of a flapper may be communicated wirelessly or through a wired connection to a respective electronics stack and/or servers 112*a-c* for the purpose of notifying a user that sampling is taking place or the possibility that tampering was detected, for example. A flapper, in embodiments may have an electrical connection-type sensor that can determine if the flapper is closed by the presence of a completed circuit within the sensor, this is merely an example as any contact sensor or grouping of sensors may accomplish this task.

For example, and with continued reference to FIG. 2, air may enter housing 204 and travel over an enclosed particle sensor 216 and chemical sensor 220 laminarly so that particle sensor 216 and chemical sensor 220 may sample the air. Laminar flow may be defined as non-turbulent flow with smooth streamlines and little to no mixing of layers of flowing particles. According to embodiments, an arrangement of particle sensor 220, chemical sensor 224, and/or any other sensors that may be present alone or in combination fully and/or partially enclosed within housing 204 may be sequential such that airflow is sampled by sensors in the order in which the sensors are reached by the airflow.

According to embodiments, and further referring to FIG. 2, housing 204 may include mounting hardware 212 for mounting detection unit 144 in a plurality of orientations and/or in a plurality of locations. Mounting hardware 212 may include threaded holes, clearance holes, hooks, slots, or other hardware interfaces that may accept or interact with standard hardware for mounting in a plurality of arrangements and orientations. In the exemplary embodiment FIG. 2A mounting hardware 212 may be arranged for mounting on a wall of a room. This is only an example and one of ordinary skill in the art would understand mounting hardware 212 may take another form for mounting the device on a ceiling or in a vehicle. Configuration of housing of entry unit 116, communication hub 172, repeater, and/or other elements of system 100 may be affected similarly.

According to embodiments, and with further reference to FIG. 2, housing 204 and enclosed components may also be configured in line with an air filtration system, a vehicle air system, an HVAC system, an air conditioning system, or any system which passes air and/or gaseous fluid through it. In embodiments, detection unit 200 may be configured to be only a subcomponent or process in a larger system such that it may detect information about a detection event and convey that to a larger system. These systems, both system 200 and the larger HVAC-type system, may be disposed in or on residential or commercial buildings, vehicles like airplanes, cars, and/or trucks, or any combination thereof, to name a few. Housing 204 may also comprise a screen configured to provide general information about the system, warnings or alerts, and/or health-related information configurable by a user or as reflected by sensor data from system 100.

With reference to FIG. 2B an isometric cutaway view of detection unit 144 from FIG. 2A is shown. The disposition of previously shown sensors 216, 220, 224, may alternatively be found within or on the device as well. In FIG. 2B electronics stack 236 is shown along with battery 228 and alarm 232. One of ordinary skill in the art would understand that the arrangement of components within housing 204 are example embodiments and in other embodiments may take different forms allowing for different shaped housings, airflow directions, mounting arrangements, and environment 108 locations.

Referring again to FIG. 1, aerosolized substance detection system 100 and/or any unit thereof, including without limitation entry unit 116, detection unit 144, communication hub 172, repeater node 176, or the like may include a display such as, for example, a light-emitting diode (LED) display, liquid crystal display (LCD), electronic ink display, cathode ray tube (CRT) display, organic LED display, or any combination thereof. According to embodiments, display may be configured to display one or more alerts, measures and/or levels detected by sensor suit, battery 132 level (especially low battery 132), a temperature of environment 108, a humidity of environment 108, general health information, or any combination thereof.

In operation, entry unit 116, detection unit 144, repeater node 176, and the communication hub 172, may be configured to enable communication between any of entry unit 116, detection unit 144, repeater node 176, and the communication hub 172. This configuration may form a network of sensors that may be distributed in a variety of configurations best suited to the detection application. Communication hub 172 may act as a gateway for transmitting data to and from the cloud to nodes. Data transmitted to the cloud may be delivered to electronic device applications used to provide alerts, view data, system status including battery power, system maintenance messages, user access, or thresholding. Repeater node 176, where present, may receive and re-transmit data to other nodes. Alternatively, some node configuration files, such as firmware, may be transmitted directly to the devices from the cloud as required.

Still referring to FIG. 1, entry unit 116 may act as a primary trigger for system 100. When a triggering event such as movement is detected, entry unit 116 may send a signal to detection unit 144s and/or units directly or via communication hub 172 and/or repeater node 176 to wake up sensors; detection unit 144 may then power on for some time and transmit data to another element, such as without limitation communication hub 172, server, and/or the cloud. Signal may then be transmitted from the cloud to an electronic device for processing. Signal from sensors may be compared to thresholds set in any unit of system 100, a server, and/or an application operating on a mobile device in communication with system 100, and if the signal exceeds the threshold an alert may be generated as a result. Thresholding algorithm may be stored, in a non-limiting example, at nodes and/or units of system 100 on firmware; in this case data processing may be done locally. In the above-described version only alerts may be transmitted to the cloud then to servers 112a-c, electronic device application, such as mobile device applications, or the like. Algorithms to determine alert states may also be more advanced to include smoothing, peak picking, and/or second derivative calculations or machine learning to train the sensors to an environment 108. Any unit of system 100, node of system 100, server, and/or mobile device in communication therewith may also receive warnings when a battery 132 in system 100 requires charging or if systems 100 is tampered with or disabled for any reason.

With further reference to FIG. 1, baselines and/or thresholds may be calculated and/or dynamically set as at any unit of system 100 as follows. A timer such as a watchdog timer, as described above, may turn on entry unit 116, detection unit 144, and/or other elements of system 100 at a configurable time to collect baseline data from sensors of sensor suite 148 at a regular interval, such as each day; any such element or combination thereof may be powered on for a configurable period of time, which may as a non-limiting example fall between 10 minutes and 60 minutes. A mean from data of each sensor, excluding zeros, and a standard deviation from the data of each sensor may then be calculated. A threshold may be established by adding a calculated mean value from each sensor to a calculated standard deviation of that sensor. A confidence factor may be applied by multiplying a standard deviation by a factor as well. Alternatively, a calculated mean value may be multiplied by a configurable variable then added to a calculated standard deviation to reduce influence of environment 108 noise. A confidence factor may be applied by multiplying standard deviation by a factor as well. In a non-limiting example, confidence factor may be calculated according to the following equation:

Baseline Threshold=Particle Count$_{Mean}$+(Variable×σ)
Alternative

Baseline Threshold=(Variable×Particle Count$_{Mean}$)+(Variable×σ)

A resulting value may be stored in the system until the next watchdog timer event. In this embodiment for 24 hours, and/or until the next configurable wakeup for baseline collection.

In an embodiment, detection unit 144 is a wearable monitoring system for vaping, cigarette smoke, fire, and/or indoor air quality (e.g. $CO_2$, CO, etc.). In this embodiment the detection unit 144 may be worn on a person and connected directly to an electronic device such as a mobile device, server, and/or communication hub 172 using any form of communicative connection, including via wireless connections such as WiFi, radar, ultrasonic, mesh, ZigBee, or Bluetooth and/or cellular connections such as 4G, LTE, 5G, RF point-to-point, or ultra wideband radio or the like for data transmission monitoring and alerting. In embodiments, wearable detection unit 144 may be connected to the cloud via wireless or cellular connection then data is transmitted from the cloud via wireless or cellular to an electronic device for monitoring and alerting. As a further non-limiting example, detection unit 144 also may contain a Radio-frequency identification (RFID) tag that is read by an electronic device such as a mobile phone or a separate RFID receiver. Alternatively, detection unit 144 may contain a global positioning system (GPS) used to monitor a location of detection unit 144. Detection unit 144, when deployed as a wearable device, may include any element and/or component used in any unit of system 100 as described above. Wearable detection unit 144 may include, for instance, one or more vents, sensor suite 148, electronics stack 128, camera 180, or the like. Wearable detection unit 144 may perform preconfigured threshold comparisons between sensed substances 104 and a preconfigured threshold to identify detection events. A wearable detection unit 144 can be used as an environment 108 surveillance tool in an area such as an industrial building or a school. A bar code, serial number, device name, QR code, or similar technology, may be used to register wearable detection unit 144 to a person wearing the node and/or another system such as a personnel database or time management system. Alerts generated from detection unit 144 are received at the electronic device and include, but are not limited to, wearable device metadata, which may include any metadata as described above, the person registered with the detection unit 144, and location.

Figure 3A:
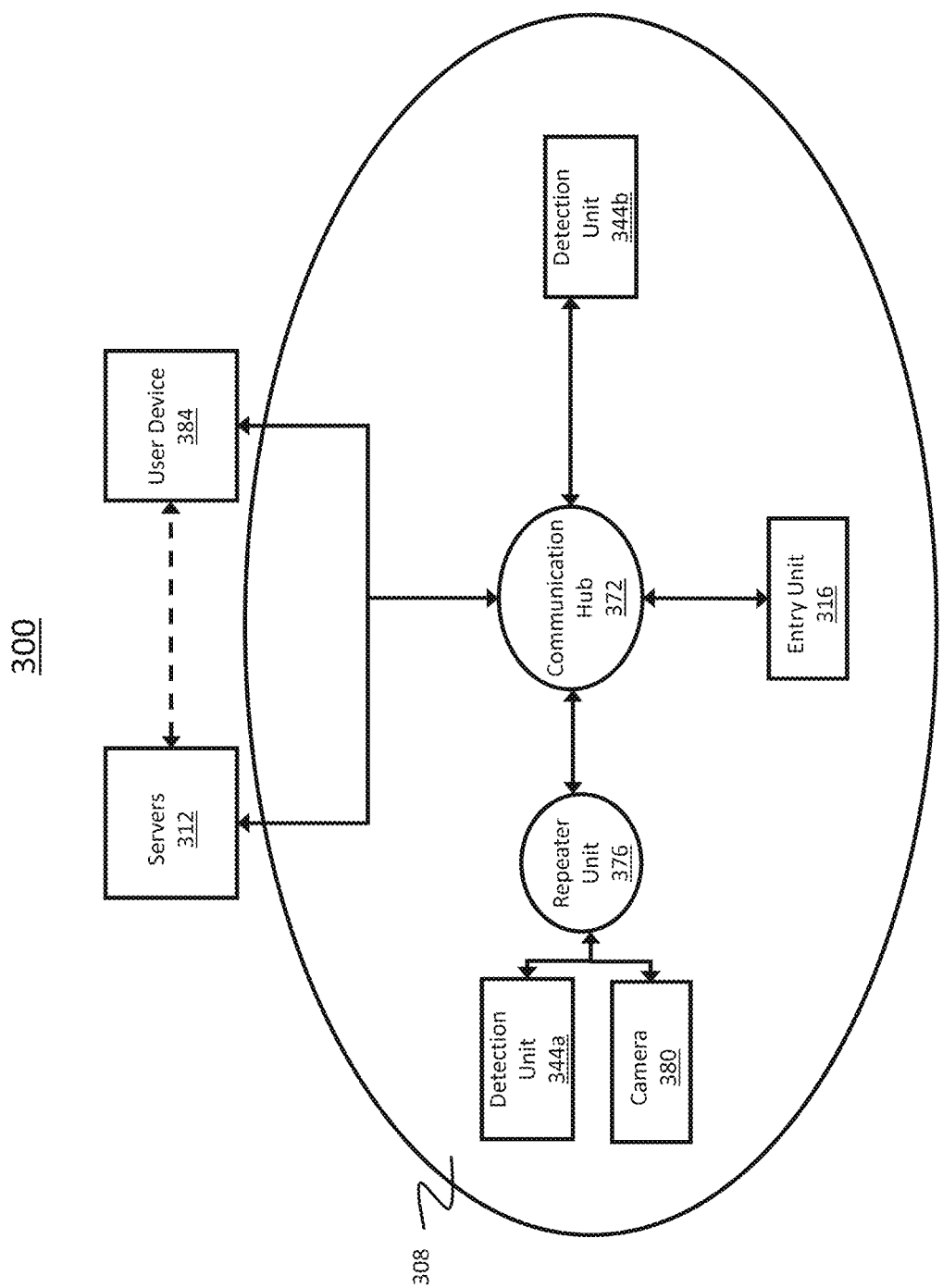
FIGS. 3A-B are block diagrams illustrating architectures for an aerosolized substance detection system, according to example embodiments.

FIGS. 3A and B illustrate example architectures 300 for vaporized aerosol detection system 100, according to embodiments. Referring now to FIG. 3A, an example architecture 300 can include entry unit 316, the same or similar as entry unit 116; repeater unit 376, the same or similar as repeater unit 176; detection units 344a,b each the same or similar as detection unit 144; camera 380, the same or similar as camera 180; communication hub 372, the same or similar as communication hub 172, or any combination thereof. In embodiments, architecture 300 can include entry unit 316, repeater unit 376, detection units 344a,b, camera 380, communication hub 372, or any combination thereof each disposed within environment 308 at two or more discrete locations within environment 308, the same or similar as environment 108.

Still referring to FIG. 3A, in an embodiment, entry unit 316 may be disposed at a first location within environment 308 and can be configured to detect when one or more objects enter environment 308. In response to detecting an object has entered environment 308, entry unit 316 may be configured to generate a detection signal and transmit the generated detection signal to communication hub 372 disposed at a second location within environment 308. In embodiments, entry unit 316 may transmit the detection signal to communication hub 372 via WiFi, a LAN, Bluetooth, ZigBee, ethernet, the internet, RF waves, near-field communication (NFC), or any combination thereof, to name a few.

In response to receiving a detection signal, communication hub 372 may be configured to analyze, such as by an electronics stack, the detection signal by, for example, comparing the detection signal to a predetermined threshold value. In some embodiments, communication hub 372 may transmit the detection signal to servers 312, the same or similar as servers 112*a-c*, configured to analyze the detection signal and transmit the result of the analysis to communication hub 372.

Based upon the analysis, communication hub 372 may further be configured to provide power to at least a portion of detection unit 344*a* and camera 380 disposed at a third location within environment 308 and detection unit 344*b* disposed at a fourth location within environment 308. In embodiments, providing power to at least a portion of detection units 344*a,b* and camera 380 can include transmitting one or more signals to power management circuitry communicatively coupled to detection units 344*a,b* and camera 380. In response, said power management circuitry can be configured to power at least a portion of detection units 344*a,b* and camera 380 from respective batteries coupled to detection units 344*a,b* and camera 380. In embodiments, providing power to at least a portion of detection units 344*a,b* and camera 380 can include switching each of detection units 344*a,b* and camera 380 from a sleep mode to an active or armed mode.

In embodiments, communication hub 372 can be configured to send and receive one or more signals to detection unit 344*a* and camera 380 via repeater unit 376. Repeater unit 376 may act as an intermediary between detection 344*a*/camera 380 and communication hub 372 such that repeater unit 376 is configured to receive incoming signals from communication hub 372, detection unit 344*a*, and/or camera 380 and transmit these incoming signals to communication hub 372, detection unit 344*a*, and/or camera 380.

According to embodiments, once at least a portion of detection units 344*a,b* are powered, they may be configured to measure one or more particle counts proximate to their respective locations within environment 308. Further, detection units 344*a,b*, may be configured to transmit these measurements to communication hub 372.

In embodiments, once at least a portion of camera 380 is powered, camera 380 may be configured to capture one or more pictures and/or videos of an area within environment 308 proximate to the respective location of camera 380. Further, camera 380 may be configured to transmit these pictures and/or video to communication hub 372.

In some embodiments, in response to receiving measures of one or more particle counts, communication hub 372 may be configured to determine if a detection event occurred proximate either to the respective locations of detection units 344*a,b*. Communication hub 372 may, for example, determine if a detection event has occurred proximate to a respective location by comparing a measure of a particle received from a detection unit at the respective location to a predetermined threshold value. In other embodiments, communication hub 372 may be configured to transmit any received measures of particle counts to servers 312. Servers 312 may be configured to determine if a detection event occurred proximate either to the respective locations of detection units 344*a,a*. Servers 312, may for example, determine if a detection event has occurred proximate to a respective location by comparing a measure of a particle received from a detection unit at the respective location to a predetermined threshold value.

When communication hub 372 and/or servers 312 have determined that a detection event has occurred, communication hub 372 and/or servers 312 can be configured to generate an alarm signal. In embodiments, the alarm signal can be transmitted to an alarm disposed near and/or proximate to the detection unit 344 that took a measurement of a particle count. The alarm signal can comprise a signal configured to induce an audible, visual, and/or tactile alert in said alarm.

According to other embodiments, the alarm signal can be transmitted to servers 312 and can comprise a signal representing the location where the detection event occurred, the time the detection event occurred, measurements taken by one or more detection units 344, a chemical make-up of the detection event, or any combination thereof. Servers 312 may be configured to transmit the alarm signal to one or more user devices 384 such that at least a portion of the information represented by the alarm signal is displayable on user device 382. User device 384 can comprise a computer, a smartphone, a tablet, a processor, a smartwatch, or any combination thereof, to name a few.

In embodiments, user device 384 can be configured to generate and transmit one or more threshold, activation, and/or deactivation signals to servers 312 and/or communication hub 372. Threshold signals can comprise signals configured to adjust, set, or modify a predetermined threshold used by entry unit 316, detection unit 344, camera 380, communication hub 372, or servers 312. Activation signals can comprise signals configured to switch a respective entry unit 316, detection unit 344, camera 380, and/or alarm to an active and/or on mode. Deactivation signals can comprise signals configured to switch a respective entry unit 316, detection unit 344, camera 380, and/or alarm to a sleep, off, and/or debug mode. Servers 312 and/or communication hub 372 may transmit received threshold, activation, and/or deactivation signals to a respective entry unit 316, detection unit 344, camera 380, and/or alarm. In embodiments, user device 384 can be configured to transmit threshold, activation, and/or deactivation signals to a respective entry unit 316, detection unit 344, camera 380, and/or alarm via WiFi, ethernet, a LAN, Bluetooth, ZigBee, NFC, Piconet, RFID, or any combination thereof.

Figure 3B:
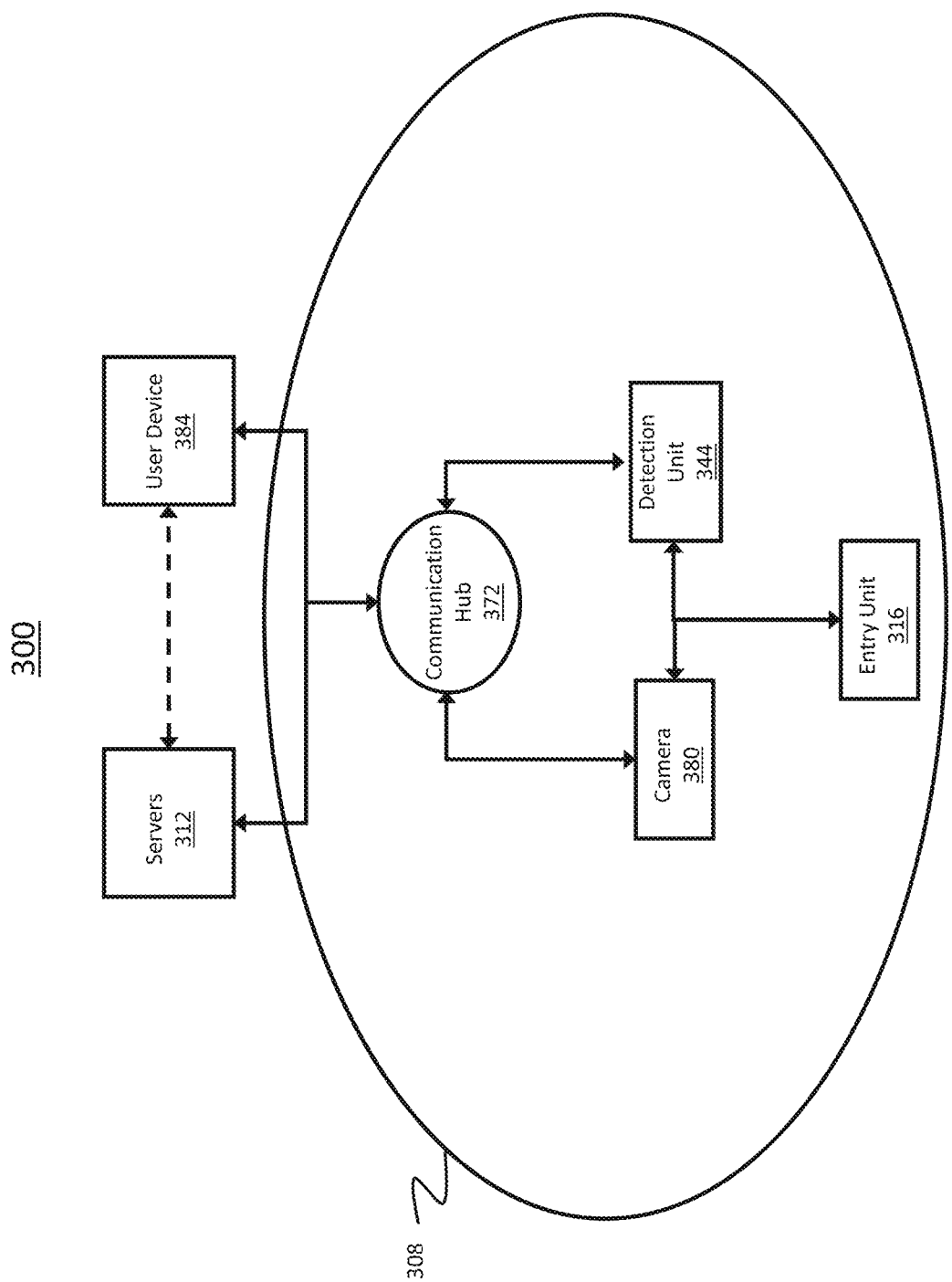

Referring now to FIG. 3B, entry unit 316 disposed at a first location within environment 308 may be configured to transmit a detection signal directly to camera 380 disposed at a second location within environment 308 and/or detection unit 344 disposed at a third location within environment 308. Entry unit 316 may transmit the detection signal to camera 380 and/or detection unit 344 by ad-hoc communications such as RFID, Bluetooth, ZigBee, Piconet, NFC, or any combination thereof, to name a few examples.

In embodiments, when camera 380 and/or detection unit 344 each receive a detection signal, at least a portion of each camera 380 and/or detection unit 344 may be powered by a respective battery. Furthermore, each of camera 380 and/or detection unit 344 may be configured to switch from a sleep or standby mode to an active mode when a detection signal is received.

According to embodiments, once at least a portion of detection units 344 is powered, it may be configured to measure one or more particle counts proximate to its respective location within environment 308. Further, detections unit 344 may be configured to transmit these measurements to communication hub 372. In embodiments, once at least a portion of camera 380 is powered, camera 380 may be configured to capture one or more pictures and/or videos of an area within environment 308 proximate to the respective location of camera 380. Further, camera 380 may be configured to transmit these pictures and/or video to communication hub 372.

Figure 4:
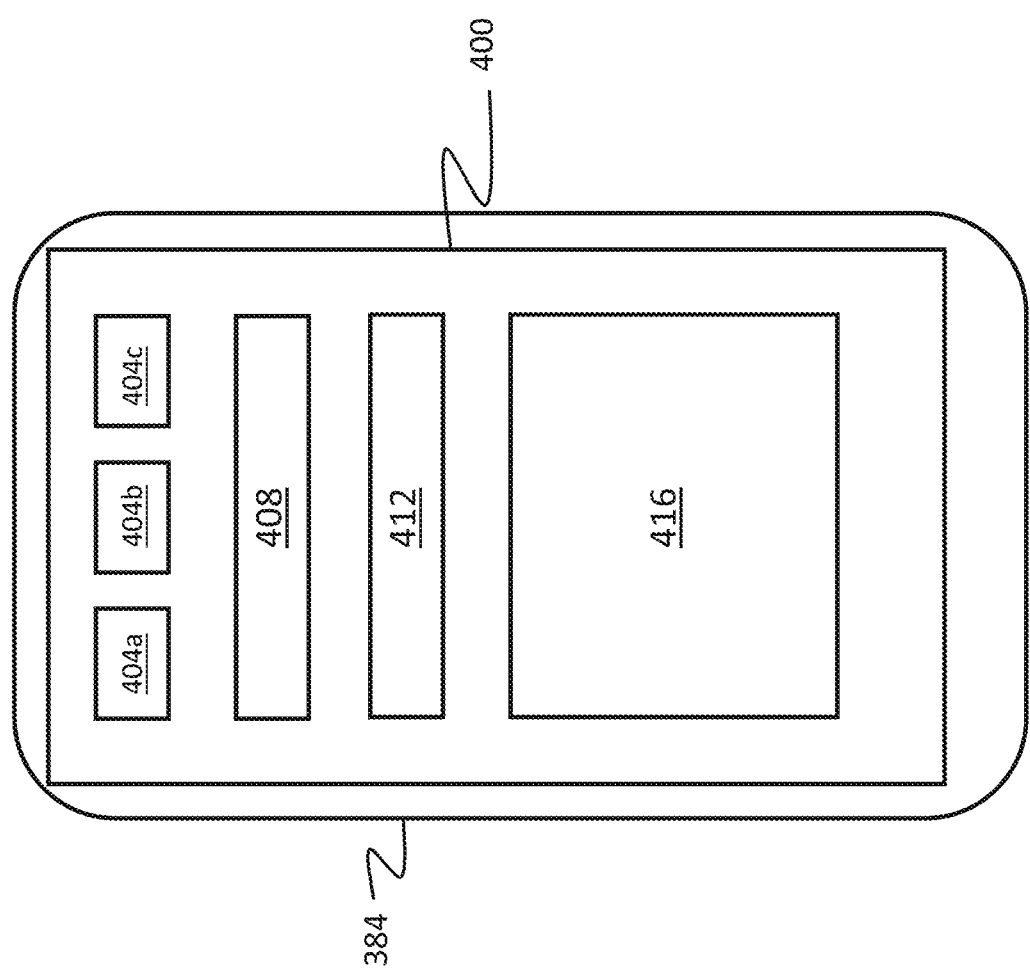
FIG. 4 is a graphical user interface on a user device for an aerosolized substance detection system, according to an example embodiment.

Referring now to FIG. 4, graphical user interface (GUI) 400 for user device 384 is presented, according to an example embodiment. GUI 400 can comprise an interactive GUI 400 that includes navigation buttons 404a-c, location selection 408, alert 412, and current window 416.

Navigation buttons 404a-c can comprise interactive buttons having a shape (e.g. oval, rectangle, circle, square, etc.) and a text representing one or more windows, sites, and/or menus associated with GUI 400. For example, navigation button 404a can include text representing a dashboard window, navigation button 404b can include text representing a readings window, and navigation button 404c can include text representing a settings window. In embodiments, navigation buttons 404a-c can each be configured to receive an interaction with GUI 400 such as a tap on a touchscreen, a swipe on a touchscreen, a mouse click, a keyboard entry, or any combination thereof, to name a few. In response to receiving an action with navigation buttons 404a-c, GUI 400 may be configured to present a window in current window 416 according to which navigation button 404 received an interaction. For example, if navigation button 404b including text representing a readings window receives an interaction, GUI 400 may be configured to present a readings window in current window 416.

Current window 416 may be configured to present information related to a window presented by GUI 400. For example, current window 416 may be configured to present information related to a dashboard window, a readings window, and/or a settings window. Information related to a dashboard window may comprise power levels of batteries associated with entry units, detection units, cameras, and/or communication hubs within a system vaporized aerosol detection system 100, alerts associated with entry units, detections units, cameras, and/or communication hubs within a system vaporized aerosol detection system 100, and/or maintenance alerts associated with entry units, detections units, cameras, and/or communication hubs within a system vaporized aerosol detection system 100. Information related to a settings window can include selectable, modifiable, and/or interactive thresholds associated with entry units, detections units, cameras, and/or communication hubs within a system vaporized aerosol detection system 100; selectable, modifiable, and/or interactive activation signals generated with entry units, detections units, cameras, and/or communication hubs within a system vaporized aerosol detection system 100; and/or selectable, modifiable, and/or interactive deactivation signals associated with entry units, detections units, cameras, and/or communication hubs within a system vaporized aerosol detection system 100.

Information related to a readings window may include measurements taken by one or more detection units such as particle counts, chemical make-ups, particle sizes, etc. Such information can be presented as dials, graphs, numbers, animations, or any combination thereof. In embodiments, the readings window can be configured to display measurements associated with a first location provided by a detection unit in or proximate to that location. According to embodiments, this first location may be indicated by location selection 408. Location selection 408 can include interactive buttons, drop-down menus, lists, and/or sliders each having text representing one or more locations within an environment. Location selection 408 can be configured to receive an interaction with GUI 400 such as a tap on a touchscreen, a swipe on a touchscreen, a mouse click, a keyboard entry, or any combination thereof, to name a few. In response to receiving an action with location selection 408, GUI 400 may change the location indicated by location selection 408 according to the received interaction. Such locations may include areas of an environment such as specific offices, classrooms, bathrooms, sectors, etc.

Alert 412 can include a window presenting whether an alert has occurred. For example, alert 412 can include text representing that a detection event has occurred, the time of the detection event, the location of the detection event, and/or the frequency of a detection event. In embodiments, alert 412 may be configured only to present alerts for detection events that occur in locations indicated by location selection 408.

Figure 5:
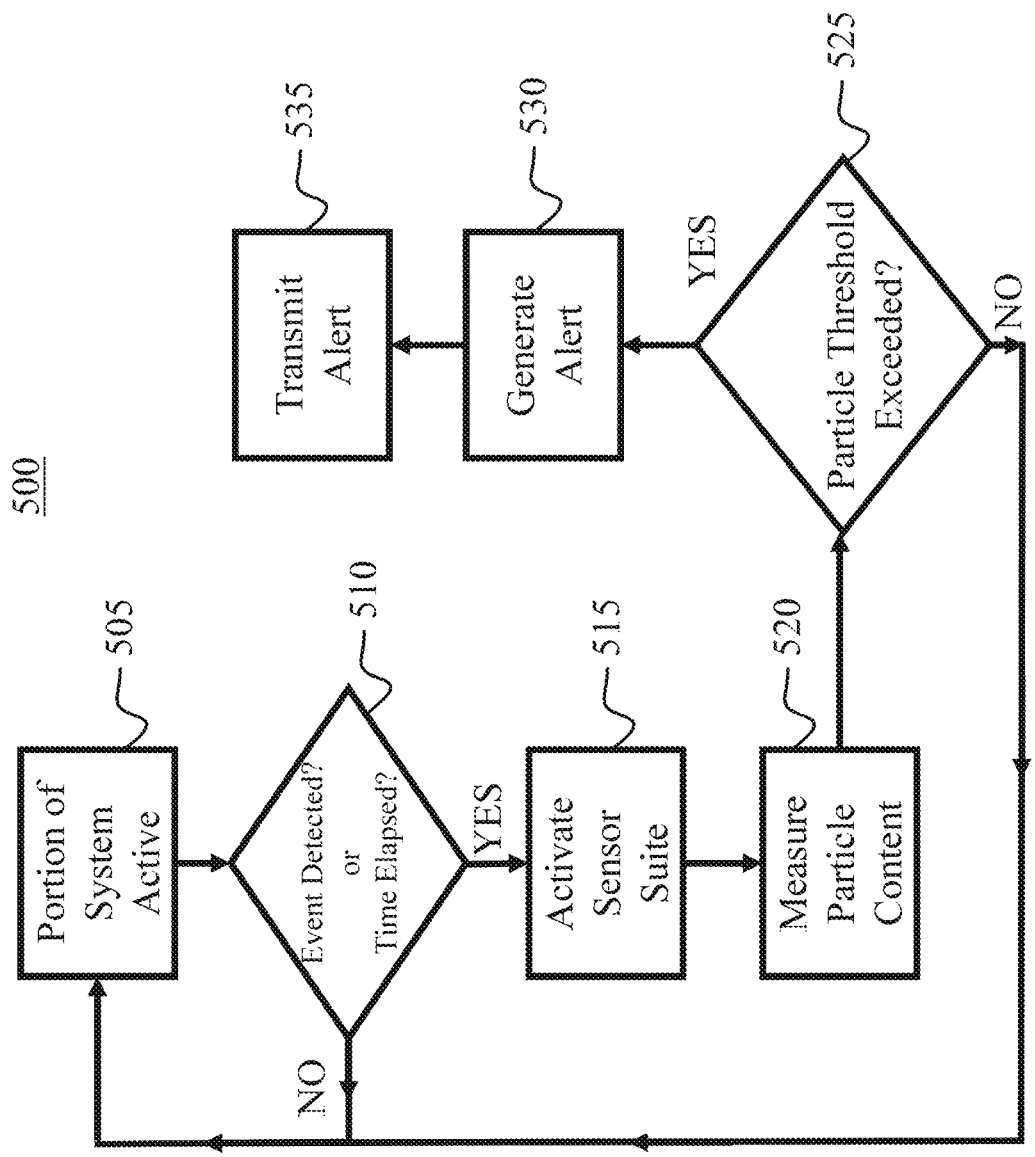
FIG. 5 is a flow chart illustrating a method for an aerosolized substance detection, according to embodiments.

With reference to FIG. 5 a flow chart illustrating a method for vaporized aerosol detection 500 is presented. At step 505, a trigger sensor, such as a motion sensor, particle sensor, chemical sensor, and/or real time clock similar or the same as motion sensor 120, particle sensor 152, or chemical sensor 156, respectively, may be active, for instance and without limitation in entry unit 116, detection unit 144, or the like. According to an embodiment, at 510, the trigger sensor may be configured to detect a triggering event. For example, a motion sensor 120 of entry unit 116 may be configured to determine whether motion has been detected by detecting motion, proximity, and/or presence of one or more objects 124a-b within a first area or location of an environment 108. In embodiments, detecting whether a triggering event has been detected in an environment 108 may include comparing captured measurements (such as motion, proximity, presence, size, speed, or any combination thereof) to a threshold value. In this way, certain types of measurements (such as motion from small animals) may be filtered out while other types of measurements (such as movement from a person walking) will be detected. In another embodiment, a similar methodology may be followed with a chemical sensor similar to or the same as chemical sensor 156, for instance and without limitation as incorporated in detection unit 144. A Chemical sensor may additionally or alternatively be powered on and upon detection of a substance of interest, may provide similar signals as motion sensor 120 configured to power the system as described below. In yet another example embodiment, a similar methodology may be followed with a particle sensor similar to or the same as particle sensor 152, such as without limitation, a particle sensor incorporated in detection unit 144. A particle sensor may additionally or alternatively be powered on, and upon detection of a substance of interest, may provide similar signals as motion sensor 120 or chemical sensor 156 configured to power the system as described below. Additionally, or alternatively, a real time clock and/or watchdog timer, which keeps track of time, may be used as a timer to power system and/or one or more units therein and/or components thereof on and off at predetermined times or intervals to perform a polling cycle, as discussed above with reference to FIG. 1.

Further referring to FIG. 5, at step 510, if a triggering event has been detected such as when motion has been detected, particles have been detected, chemicals have been detected, and/or a predetermined time has elapsed or arrived then the system moves on to step 515, otherwise step 505 is repeated. At 515, a portion of the system at a second location of environment 108, which may correspond to at least a portion of a sensor suite 148 similar or the same as sensor suite 148 is activated; for instance, and without limitation, at least a detection unit 144 may be activated upon receipt of a signal from entry unit 116. Step 515 may include powering a portion of sensor suite 148 and arming constituent sensors. Arming of sensors at step 515 may also command those sensors to begin taking measurements. Arming of sensors may be irrespective of readings of any sensors, in other words, if a triggering event is detected at step 510, a sensor suite 148 may start taking measurements with or without the presence of vaporized aerosols.

At step 520, and still referring to FIG. 5, a particle count of environment 108 is measured by sensor suite 148 of detection unit 144. Sensor suite 148 may be configured to detect a quantity, size, density, composition, structure, dispersion, or any combination thereof, of aerosolized particles in vaporized aerosol in a certain area similar or the same as environment 108. In embodiments, sensor suite 148 may be configured to generate one or more signals including data representing quantity, size, density, composition, structure, dispersion, or any combination thereof of aerosolized particles. According to embodiments, these signals may be sent to another device and/or component such as communication hub 172, one or more servers 112*a-c*, a mobile device, or the like.

At step 525, and with continued reference to FIG. 5, system 100 may be configured to determine whether a detection event has occurred. Determining whether a detection event has occurred may include determining a presence of substances 104 of interest in an area. Substances 104 of interest may include any substances 104 that may be a cause of concern for an area. For example, substances 104 of interest may include substances 104 that are disallowed in an area (such as nicotine, cannabinoids, tetrahydrocannabinoids, tobacco smoke, etc.), particles that are hazardous (carbon monoxide, arsine, hydrogen azide, hydrogen cyanide, nitrogen dioxide, viruses, bacteria, pathogens, etc.), undesirable particles for the area (tobacco smoke, nicotine, cannabinoids, tetrahydrocannabinoids, ammonia from pet excrement, etc.), or any combination thereof, to name a few. According to embodiments, determining presence of substances 104 of interest may include comparing, respectively by a unit and/or component of system 100, such as without limitation an electronics stack 128, entry unit 116, detection unit 144, communication hub 172, and/or at least a server, a detected size, structure, composition, density, and/or dispersion to a threshold value. For example, a detected size exceeding a threshold value may indicate that substances 104 of interest are present in an area.

Further referring to FIG. 5, at 525, system 100 may be configured to compare a quantity, particle density, and/or dispersion of detected substances 104 of interest to one or more predetermined threshold values in order to determine if a detection event has occurred. For example, system 100 may be configured to compare a detected particle density (such as from a cloud of aerosolized vape) to a threshold value and determine that the particle density has exceeded the threshold value indicating a detection event has occurred. If a detection event has occurred then the system moves to step 530, otherwise the system repeats step 505.

At step 530, and continuing to refer to FIG. 5, an alarm signal is generated; the alarm signal may include a signal configured to induce an alert from an alarm. An alert may include an auditory alert or signal (such as a buzzer, siren, horn, etc.), a visual alert or signal (such as an LED, strobe light, laser, LED screen, LCD screen, etc.), tactile alert or signal (such as a vibration alarm, motor, etc.), or any combination thereof.

At 535, and further referring to FIG. 5, an alarm signal may be transmitted to one or more servers (the same or similar as servers 122 *a-c*) or a user device, and additionally stored; alarm signal may alternatively or additionally be generated on the one or more servers. An alarm signal may include data indicating that a detection event has occurred in the area and may be configured to display a particle count, density, size, composition, etc. as well as the area in which the detection event occurred on the user device. A user device may include a computer, a processor, a server, a smartphone, a tablet, a laptop, or any combination thereof, to name a few. In embodiments, a user may disable an alarm from a user device, whether that alarm was triggered by a detection event or a tamper event.

With reference to FIG. 6, a flow chart illustrating a method 600 for power distribution in an aerosolized substance detection system is presented. At step 605, a trigger sensor, such as a motion sensor, particle sensor, chemical sensor, or the like, which may be similar or the same as motion sensor 120, particle sensor 152, or chemical sensor 156, respectively, may be active. At step 610, a trigger sensor may be configured to determine whether a triggering event has occurred. For example, a motion sensor may be configured to determine whether motion has been detected by detecting motion, proximity, and/or presence of one or more objects 124*a-b* within an area. Additionally, or alternatively, at 610, a particle sensor or chemical sensor may be configured to determine if vaporized aerosols and/or chemicals are present within an area. In embodiments, detecting whether motion has been detected in an environment 108 may include comparing a detected motion, proximity, presence, size, speed, or any combination thereof to a threshold value. In this way, certain types of motion (such as from small animals) may be filtered out while other types of motion (such as from a person walking) will be detected. In another example embodiment, a similar methodology may be followed with a chemical sensor similar to or the same as chemical sensor 156. A chemical sensor may be powered on, and upon detection of a substance of interest, may provide similar signals as motion sensor 120 configured to power the system as described below. In yet another example embodiment, a similar methodology may be followed with a particle sensor similar to or the same as particle sensor 152. A particle sensor may additionally or alternatively be powered on, and upon detection of a substance of interest, may provide similar signals as motion sensor 120 or chemical sensor 156 configured to power the system as described below. Additionally, or alternatively, a real time clock, which keeps track of time, may be used as a timer to power the system on and off at predetermined times or intervals.

Further referring to FIG. 6, at step 610, and in separate or the same example embodiments, if a triggering event such as when motion has been detected, particles have been detected, chemicals have been detected, and/or a predetermined time has elapsed or arrived then system 100 may move on to 615, otherwise 605 may be repeated. At step 615, a portion of the system 100 such as detection unit 144, may be activated. In embodiments, activating a portion of system 100, such as detection unit 144, may include providing power to one or more sensors within sensor suite 148 from a battery 132 incorporated in detection unit 144. In embodiments, power from battery 132 may be controlled and directed by a detection unit 144 electronics stack 128.

Electronics stack 128 and/or detection unit 144 may be configured to provide power to one or more sensors of the sensor suite 148 when motion, particles, chemicals, or in general, substances 104 of interest have been detected in the area. Further, in embodiments, electronics stack 128 and/or detection unit 144 may be configured to provide power from battery 132 to one or more components of electronics stack 128 and/or detection unit 144 in response to motion being detected in the area.

Figure 6:
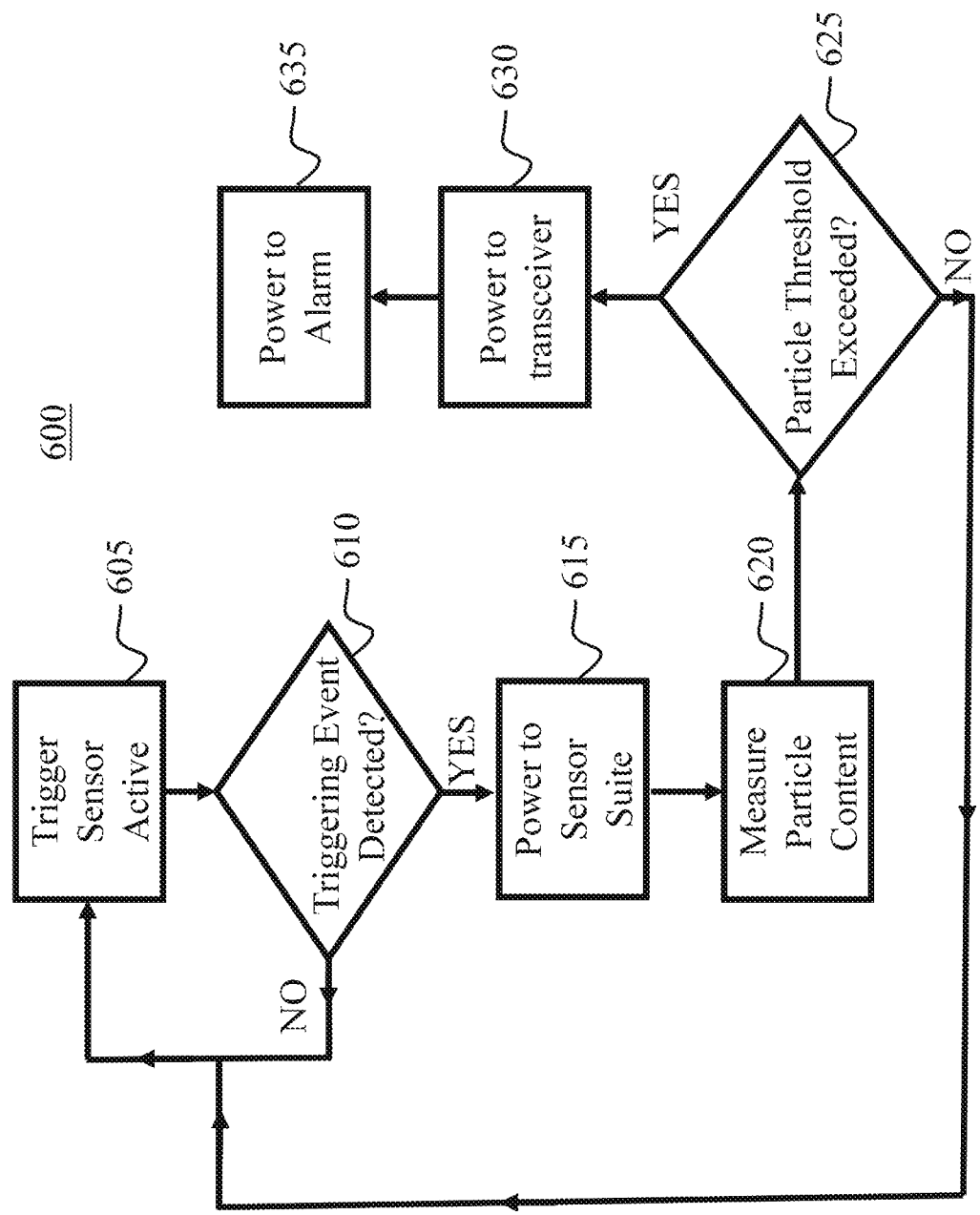
FIG. 6 is a flow chart illustrating a method of power management of an aerosolized substance detection system, according to embodiments.

Still referring to FIG. 6, at step 620, a particle count of environment 108 is measured by powered sensors within sensor suite 148. Powered sensors may be configured to detect quantity, size, density, composition, structure, dispersion, or any combination thereof, of aerosolized particles in vaporized aerosol in a certain area similar or the same as environment 108. In embodiments, powered sensors may be configured to generate one or more signals including data representing a quantity, size, density, composition, structure, dispersion, or any combination thereof of aerosolized particles. According to embodiments, these signals may be sent to a detection unit 144 electronics stack.

At step 625, and with continued reference to FIG. 6, system 100 and/or any unit and/or element thereof may be configured to determine whether a detection event has occurred. Determining whether a detection event has occurred may include determining a presence of substances of interest 104 in an area. Substances of interest 104 may include any particles that may be a cause of concern in an area. For example, substances of interest 104 may include particles that are disallowed in an area (such as nicotine, cannabinoids, tetrahydrocannabinoids, tobacco smoke, etc.), particles that are hazardous (carbon monoxide, arsine, hydrogen azide, hydrogen cyanide, nitrogen dioxide, viruses, bacteria, pathogens, etc.), undesirable particles for an area (tobacco smoke, nicotine, cannabinoids, tetrahydrocannabinoids, ammonia from pet excrement, etc.), or any combination thereof, to name a few. According to embodiments, determining a presence of substances of interest 104 may include comparing, respectively by an electronics stack and/or at least a server, a detected size, structure, composition, density, and/or dispersion to a threshold value. For example, a detected size exceeding a threshold value may indicate that substances of interest 104 are present in the area.

Further referring to FIG. 6 at step 625, network is configured to compare a quantity, particle density, and/or dispersion of detected substances of interest 104 to one or more predetermined threshold values in order to determine if a detection event has occurred. For example, a system may be configured to compare a detected particle density of carbon dioxide to a threshold value and determine that the particle density has exceeded a threshold value indicating a detection event has occurred. If a detection event has occurred then system 100 moves to 630, otherwise the system may cease providing power to the sensors and the system repeats step 605.

At step 630, and still referring to FIG. 6, power is provided from a battery to a transceiver within an electronics stack, such as without limitation an electronics stack of detection unit 144. Transceiver may be configured to transmit and/or receive data from one or more servers the same or similar to servers 112a-c and/or a user device via, for example, internet, cellular networks, WIFI, Bluetooth, ZigBee, ethernet, wired connections, or any combination thereof. A user device may include a computer, a processor, a server, a smartphone, a tablet, a laptop, or any combination thereof, to name a few.

At step 635, and with continued reference to FIG. 6, power is provided from a battery to an alarm. In embodiments, an alarm is configured to generate an alert or signal when power is provided and/or an alarm signal is received. Such an alert may include, but is not limited to, an audible alert or signal (such as a buzzer, siren, horn, etc.), a visual alert or signal (such as an LED, strobe light, laser, LED screen, LCD screen, etc.), tactile alert or signal (such as a vibration alarm, motor, etc.), or any combination thereof.

Figure 7:
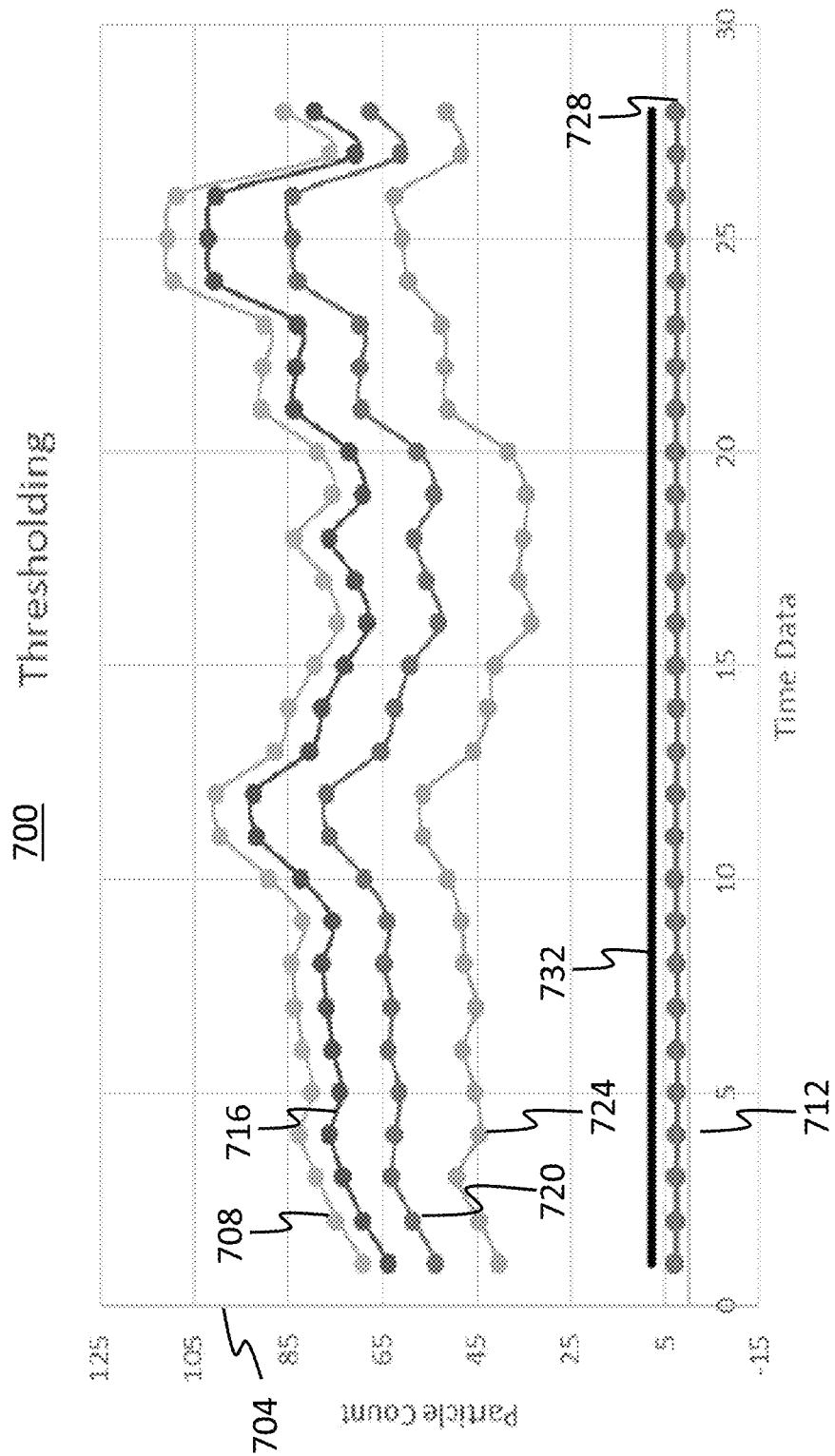
FIG. 7 is a graph representing example graphical thresholding values, according to an example embodiment.

Referring now to FIG. 7, a graph 700 representing example sensor signals 708, 716, 720, 724, and 728 and an example threshold 732 over particle count 704 vs time 712 is presented, according to an example embodiment. Graph 700 demonstrates an example particle count threshold that, when exceeded, may trigger an alarm and/or alert. According to graph 700, it can be seen that sensor signals 708, 716, 720, 724, and exceed threshold 732. Conversely, sensor signal line 728 does not exceed threshold 732 and would therefore not trigger an alarm and/or an alert due to a detection event that has occurred.

Figure 8A:
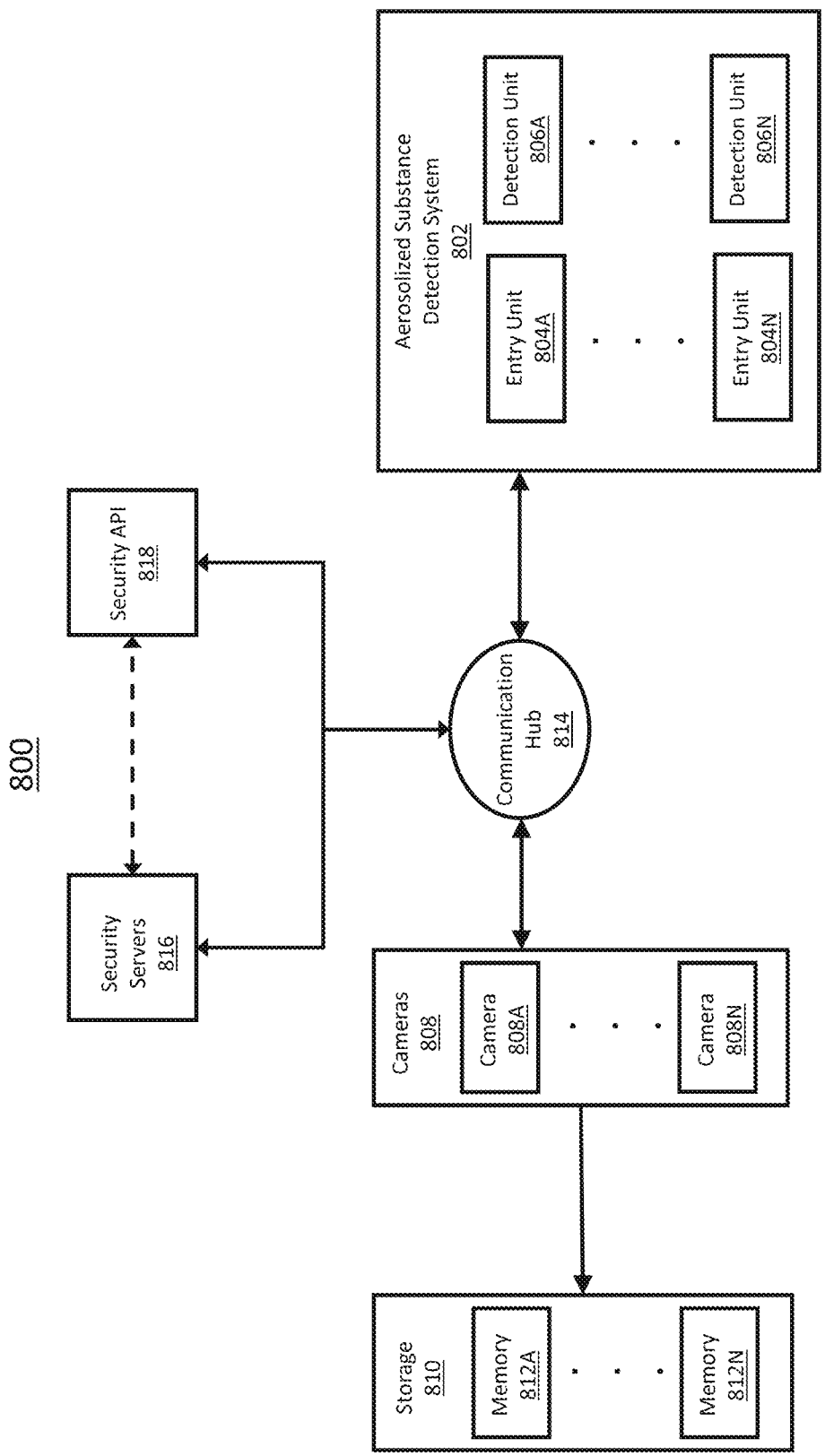
FIG. 8A is a block diagram illustrating an aerosolized substance detection system implemented in a distributed security system, according to an example embodiment.
Figure 8B:
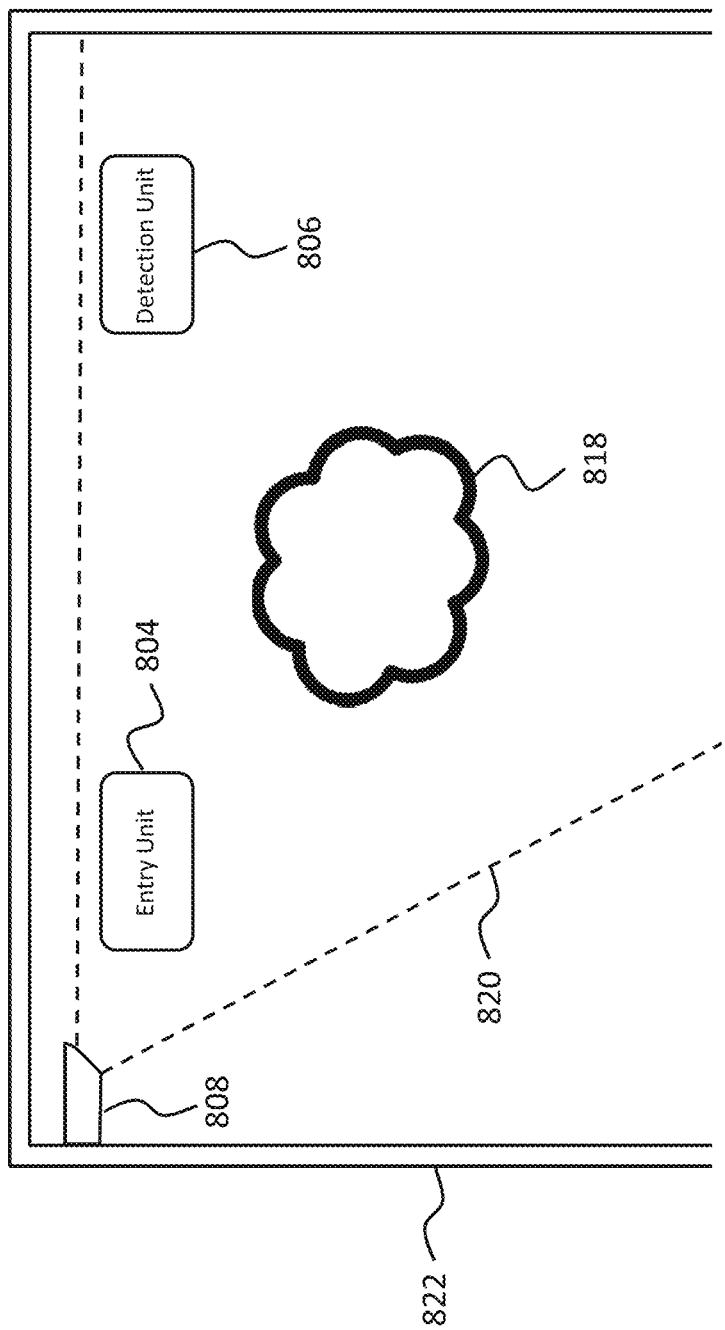
FIG. 8B is a diagram illustrating an example case of an aerosolized substance detection system implemented in a distributed security system, according to an example embodiment.

FIGS. 8A and 8B, each refer to an aerosolized substance detection system 802 implemented within or configured to work in tandem with distributed security system 800. Distributed security system 800 is configured to monitor one or more environments of interest such as schools, kennels, office buildings, and/or any environment discussed above with reference to environment of interest 108. In embodiments, monitoring may include positioning one or more cameras, similar or the same as camera 380, at one or more locations within an environment of interest to capture video and/or stills of one or more portions of the environments of interest. For example, monitoring can include positioning a first camera at a first location to capture video of a first portion of a school, such as a classroom, and a second camera at a second location to capture a second portion of the school, such as a hallway. According to some embodiments, each feed from the cameras may be viewed, singularly or concurrently, by one or more displays and/or user devices (e.g., smartphone, tablet, laptops, etc.) connected to the cameras by a closed circuit, internet, ethernet, wireless network, Bluetooth, Zigbee, ad-hoc network, communication hub, application programming interface (API), or any combination thereof, to name a few.

Referring now to FIG. 8A, a block diagram illustrating aerosolized substance detection system 802 working with distributed security system 800 is presented. According to embodiments, aerosolized substance detection system 802 may be configured to be integrated within or work in tandem within distributed security system 800 to provide aerosolized substance detection. For example, aerosolized substance detection system 802 may be integrated within distributed security system 800 to allow distributed security system 800 to take video, create alerts, create alarms, and/or log when a detection event occurs.

According to embodiments, distributed security system 800 can include cameras 808 distributed at one or more locations within an environment of interest. Each camera 808 can comprise, for example, a box camera, dome camera, pan, tilt and zoom camera, bullet camera, internet protocol (IP) camera, day/night camera, thermal (FLIR) camera, wireless IP camera, fisheye camera, or any combination thereof, configured to capture stills and/or video. According to embodiments, each camera 808 can be positioned to capture stills and/or video or at least a portion of an environment of interest. For example, each camera 808 may be disposed such that its field of vision is positioned to cover at least a portion of an environment of interest. In embodiments, distributed security system 800 can include any N number of cameras. While in the illustrative embodiment of FIG. 8A, two cameras are presented, in other embodiments, any number of cameras may be used. In some embodiments, each camera 808 may further be configured to log and transmit timestamps associated with captured video and stills. A "timestamp," as used herein, comprises data representing the time at which a specific segment, frame, or portion of video was captured or a time at which a specific still was captured. According to embodiments, a timestamp can include the year, month, week, day, hour, minute, second, or any fraction thereof, when video or stills were captured. According to embodiments, each camera 808 may further be configured to transmit identification information related to the camera 808 such as a physical location, a location within an environment of interest, a MAC address, an IP address, or any combination thereof.

In embodiments, each camera 808 may store any captured video, stills, and/or timestamps in data storage 810. Storage 810 includes one or more memories 810A-N each configured to store and recall captured video and stills. Each memory 810A-N may comprise a flash memory, hard disk drive, solid state memory, random-access memory, programmable read-only memory, electronically erasable programmable read-only memory, or any combination thereof, to name a few. According to embodiments, storage 810 may be distributed such that each memory 812 is disposed at one or more locations. Each memory 812 can be configured to be in communication with one or more other memories via the internet, ethernet, a wireless network, Bluetooth, Zigbee, ad-hoc network, communication hub, or any combination thereof, to name a few.

Likewise, each camera 808 can be communicatively coupled to one or more memories 812A-N via the internet, ethernet, a wireless network, Bluetooth, Zigbee, ad-hoc network, communication hub, or any combination thereof, to name a few. In some embodiments, each camera 808 may be configured to store captured videos and stills in a respective memory 812. For example, camera 808A may be configured to store captured videos and stills in memory 812A. A camera 808 and respective memory 812 can be disposed proximate to one another (such as to allow for ad-hoc communications) or be disposed at a same location within an environment of interest. In some embodiments, a camera 808 and respective memory 812 may be disposed within a same housing such that a camera 808 and a respective memory 812 form one unit.

In some embodiments, cameras 808A-N can be configured to transmit captured video, stills, and/or timestamps to one or more security servers 816 and/or security API 818 via the internet, ethernet, a wireless network, Bluetooth, Zigbee, ad-hoc network, or any combination thereof, to name a few. Additionally, or alternatively, cameras 808A-N can be configured to transmit captured video and/or stills to security servers 816 and/or security API 818 via communication hub 814. Communication hub 814, similar or the same as communication hub 172, can be configured to be in communication with cameras 808A-N, aerosolized substance detection system 802, security servers 816, and security API 818 and further be configured to facilitate communications between any combination thereof. In some embodiments, communications between aerosolized substance detection system 802, cameras 808A-N, security servers 816, and/or security API 818, may be encrypted such as by symmetric encryption and/or asymmetric encryption.

According to embodiments, aerosolized substance detection system 802 may be configured to detect one or more triggering events and/or detection events at one or more locations within an environment of interest. Aerosolized substance detection system 802 may include one or more entry units 804A-N, each similar or the same as entry unit 116, and one or more detection units 806A-N, each similar or the same as detection unit 144. As discussed above with reference to FIGS. 1-6, each entry unit 804 is configured to detect a triggering event at one or more location in an environment of interest. For example, each entry unit may detect when a person has entered an environment of interest or an area proximate to the entry unit. In response to detecting the triggering event, each entry unit 804 may be configured to generate a detection signal that may be sent to one or more detection units 806A-N and/or security servers 816. According to some embodiments, at least a portion of aerosolized detection system 802 may comprise a wearable device such as a sensor, user device, tablet, smart watch, smartphone, or any combination thereof, to name a few.

Further, as discussed above with reference to FIGS. 1-6, each detection unit 806 may be configured to measure, in response to the detection signal, a quantity (i.e., particle count), size, structure, dispersion, or any combination thereof, of one or more substances within an environment of interest or an area proximate to the detection unit. For example, a detection unit 806 may be configured to detect a particle count of discouraged substances within an environment of interest. In embodiments, each detection unit 806 may transit any measurements to security servers 816. Additionally, each detection unit 806 may transmit identification information related to the detection unit such as a physical location, a location within an environment of interest, a MAC address, an IP address, or any combination thereof.

According to some embodiments, and as discussed above with reference to FIGS. 1-6, each detection unit 806 may further be configured to determine that a detection event has occurred such as by determining a taken measurement to a threshold value. For example, a detection unit may compare a taken measurement of a particle court for a discouraged substance to a threshold value. Each detection unit 806 may further be configured to transmit a signal indicating that a detection event has occurred to servers 816. According to embodiments, the signal indicating that a detection event has occurred may include data representing the year, month, week, day, hour, minute, second, or any fraction thereof, when the detection event was determined.

Security servers 816 are configured to log, store, display, and/or transmit any video, stills, timestamps, detection signals, detection events, measurements, or any combination thereof received from cameras 808 and aerosolized substance detection system 802. In embodiments, security servers 816 may be configured to determine if a triggering event and/or detection event has occurred similarly or the same as servers 112 as discussed above with reference to FIG. 1. According to embodiments, security servers 816 may be configured to activate one or more cameras 808 to start taking video or stills in response to a detection signal, signal indicating a detection event, determining a triggering event has occurred, determining a detection event has occurred, or any combination thereof. Security servers 816 may also or otherwise be configured to instruct one or more cameras 808 to store any captured videos or stills in a respective memory 812 in response to a detection signal, signal indicating a detection event, determining a triggering event has occurred, determining a detection event has occurred, or any combination thereof.

In embodiments, security servers 816 may be configured to associate received and/or determined triggering events and detection events with captured video or stills from one or more cameras. Associating determined triggering events and detection events with captured video or stills may comprise storing the data in a same location, storing the data in relational tables, creating and storing pointers, concurrently displaying the information, or any combination thereof, to name a few. According to embodiments, security servers 816 may be configured to associate received and/or determined triggering events and detection events with captured video or stills according to the timestamps and physical location of the received and/or determined triggering events and detection events and the captured video or stills. For example, security servers 816 may associate a detection event received from a location A and a time X with video captured of location A and at a time X.

According to embodiments, security servers 816 may display received measurements, received video, received stills, triggering events, and/or detection events on one or more displays. A display may comprise a monitor, a user device (such as a smartphone, tablet, laptop, etc.), a webapp, or any combination thereof to name a few. In embodiments, security servers 816 may be configured to display measurements, received video, received stills, triggering events, and/or detection events within security API 818. According to embodiments, security servers 816 may be configured to display data, such as captured video, stills, and measurements, according to received an/or determined triggering events or detection events. For example, security servers 816 may display captured video and measurements concurrently with similar timestamps received from a same location when a detection event is detected at that location.

Security servers 816 may include one or more servers which may comprise any computing device as described in this disclosure, including without limitation a microcontroller, microprocessor, digital signal processor (DSP) and/or system on a chip (SoC) as described in this disclosure. Each server of security servers 816 may include, be included in, and/or communicate with a user device such as a mobile telephone or smartphone. Any server of security servers 816 may include a single computing device operating independently, or may include two or more computing devices operating in concert, in parallel, sequentially or the like; two or more computing devices may be included together in a single computing device or in two or more computing devices. Any server of security servers 816 may interface or communicate with one or more additional devices as described below in further detail via a network interface device. Network interface devices may be utilized for connecting a server to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Any server of security servers 816 may include but is not limited to, for example, a computing device or cluster of computing devices in a first location and a second computing device or cluster of computing devices in a second location. Any server of security servers 816 may include one or more computing devices dedicated to data storage, security, distribution of traffic for load balancing, and the like. Any server of security servers 816 may distribute one or more computing tasks as described below across a plurality of computing devices, which may operate in parallel, in series, redundantly, or in any other manner used for distribution of tasks or memory between computing devices.

Security API 818 comprises an application programming interface configured to interact with distributed security system 800. In embodiments, security API 818 can be configured to run a user device the same or similar as user device 384, and is configured to display, modify, store, transmit, and/or manipulate data to and from security servers 816. For example, security API may be configured to display one or more captured video feeds received by security servers 816 and may also be configured to set threshold values for triggering and detection events as discussed above with reference to FIGS. 1-6.

In embodiments, security API 818 may be configured to received one or more interactions. Interactions may comprise a swipe on a touchscreen, a tap on a touchscreen, a text entry, a mouse movement, or any combination thereof, to name a few. According to embodiments security API 818 may be configured to display, modify, store, transmit, and/or manipulate data to and from security servers 816 according to received interactions. For example, security API 818 may be configured to display or switch captured video streams according to received interactions. As another example, security API 818 may be configured to display, enlarge, and/or highlight one or more captured measurements received by servers 816 according to received interactions.

Referring now to FIG. 8B, an example implementation of aerosolized substance detection system 802 in a distributed security system 800 is presented. According to an example embodiment, distributed security system 800 can include a camera 808 disposed at an environment of interest 822 such as a school hallway. Camera 808 has a field of vision 820 positioned to capture video from at least a portion of environment of interest 822. Distributed security system 800 is configured to work with aerosolized substance detection system 802 which includes entry unit 804 and detection unit 806. Aerosolized substance detection system 802 is configured to detect when a person enters the environment of interest 822 and, in response, take a measurement of vapor cloud 818.

As an example, entry unit 804 may detect when a person enters environment of interest 822 as discussed above with reference to FIGS. 1-6. In response, entry unit 804 may generate and send a detection signal to detection unit 806 and security servers 816. In some embodiments, security servers 816 may be configured to instruct camera 808 to begin capturing video in response to receiving the detection signal. Detection unit 806 may be configured to take a measurement of particle cloud 818 in response to the detection signal as discussed above with reference to FIGS. 1-6. In some embodiments, detection unit 806 may determine that a detection event has occurred based on the taken measurement and may transmit a signal indicating a detection event has occurred to security servers 816. In other embodiments, the taken measurement may be transmitted to security servers 816 which may, in turn, determine that a detection event has occurred based on the taken measurement. According to embodiments, security servers 816 may be configured to instruct camera 808 to begin capturing video in response to receiving a signal indicating a detection event has occurred or determining a detection event has occurred.

Figure 9A:
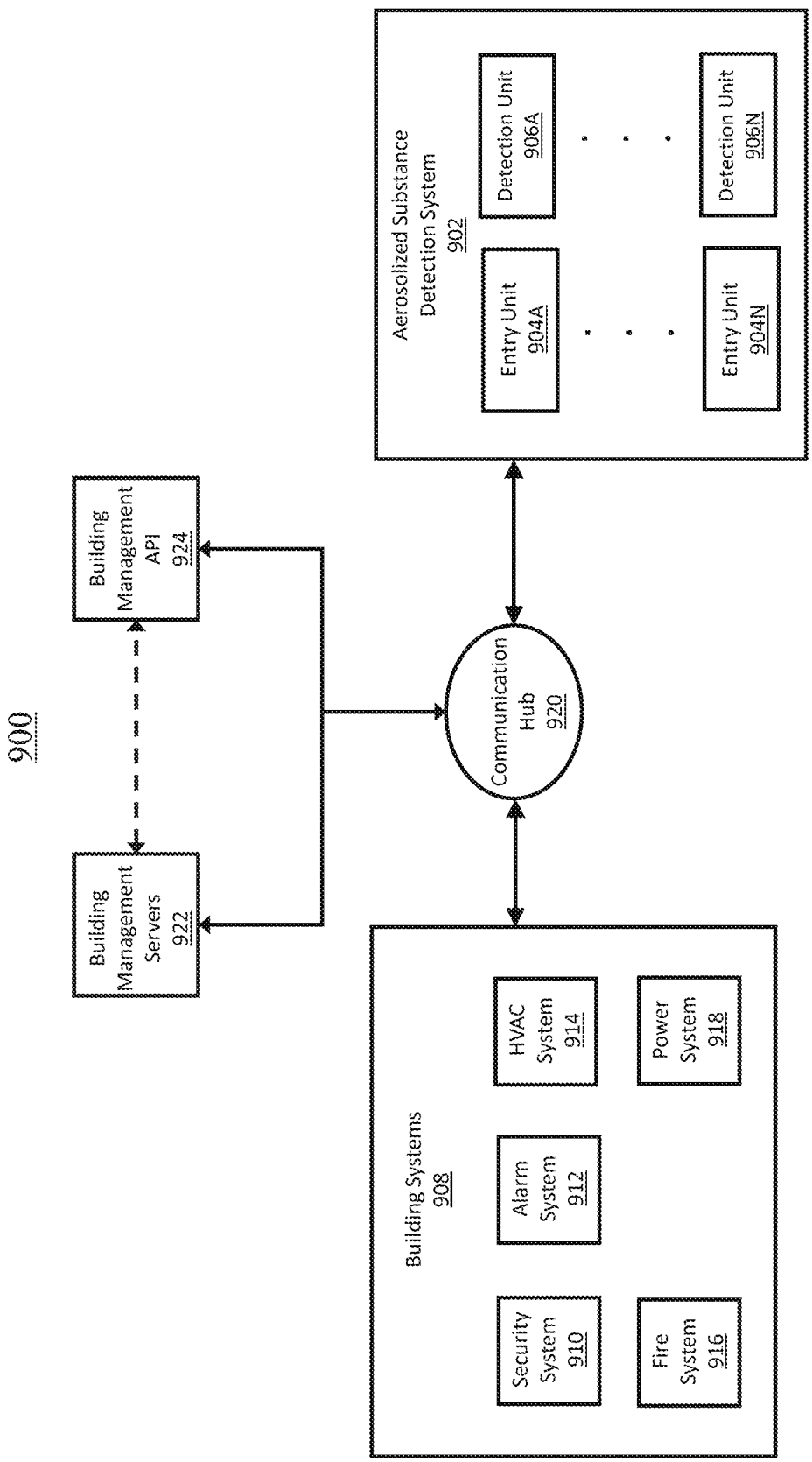
FIG. 9A is a block diagram illustrating an aerosolized substance detection system implemented in a building management system, according to an example embodiment.
Figure 9B:
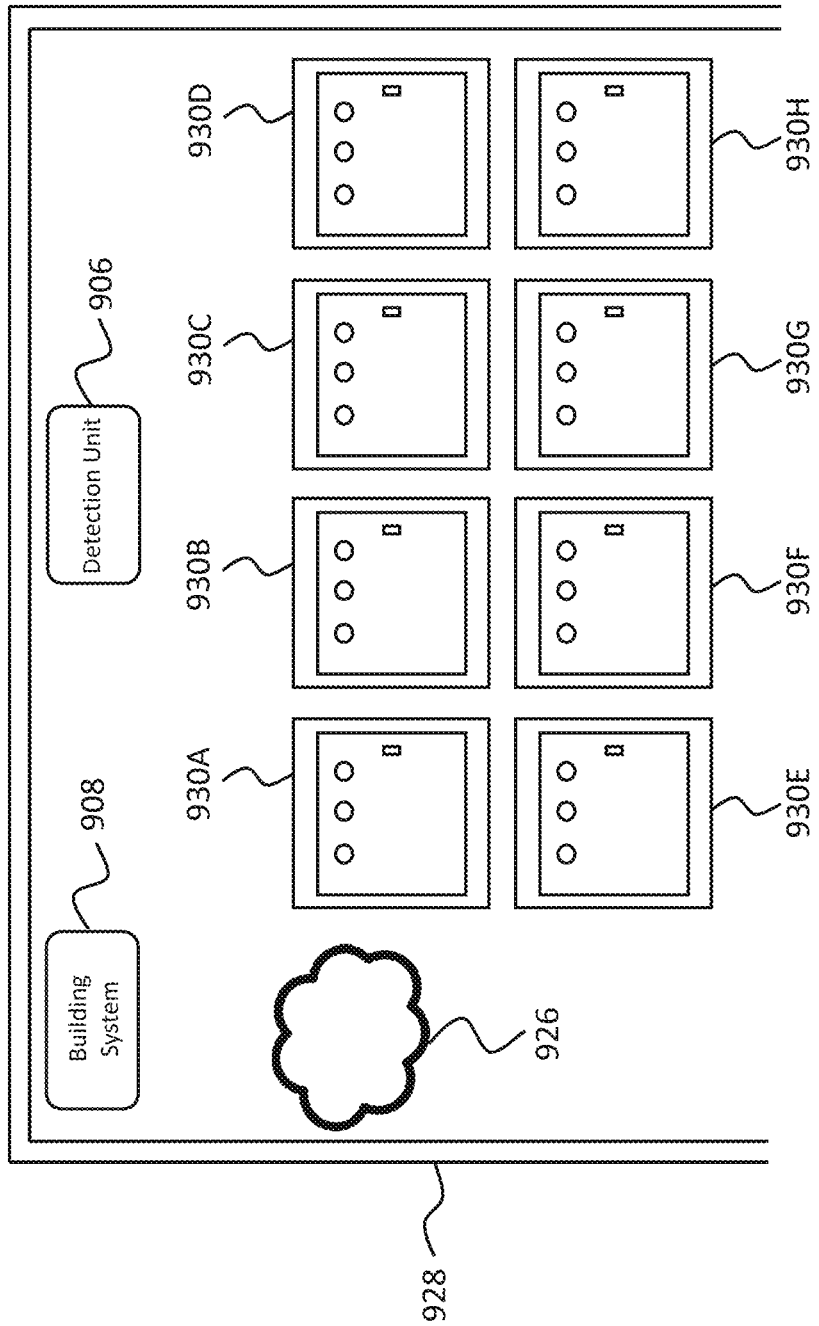
FIG. 9B is a diagram illustrating an example case of an aerosolized substance detection system implemented in a building management system, according to an example embodiment.
Figure 10:
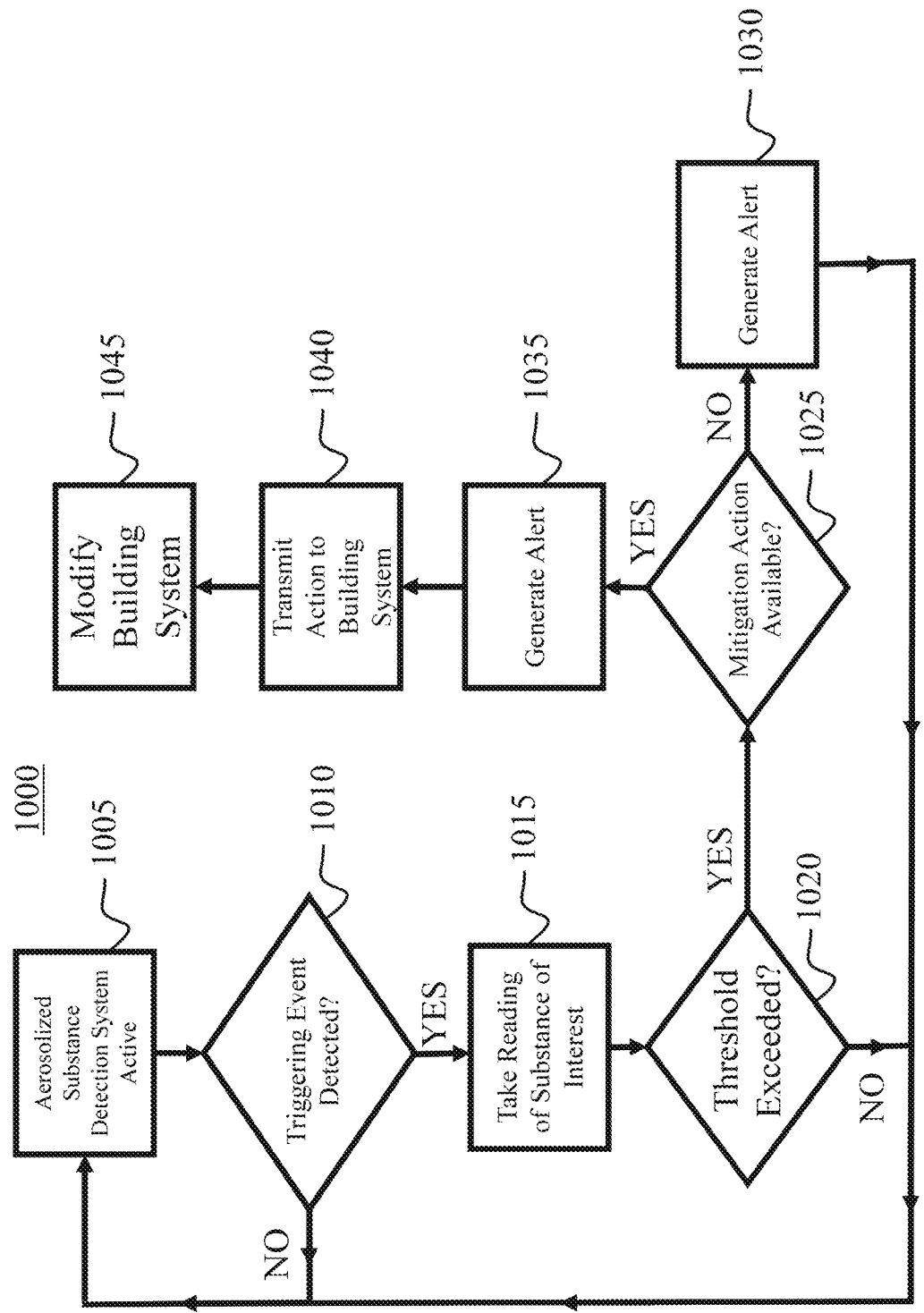
FIG. 10 is a flow chart illustrating a method for aerosolized substance detection system implemented in a building management system, according to an example embodiment.

FIGS. 9A, 9B, and 10, each refer to an aerosolized substance detection system 902 implemented within or configured to work in tandem with building management system 900. Building management system 900 is configured to monitor, modify, and toggle one or more building systems 908 of an environment of interest such as a school, kennel, office building, and/or any environment discussed above with reference to environment of interest 108. Building systems 908 can include security system 910 configured to monitor one or more areas of an environment of interest. Monitoring one or more areas of an environment of interest can include receiving, analyzing, and manipulating data from one or more cameras, similar or the same as camera 380, proximity sensors, infrared sensors, noise sensors, microphones, motion sensors, microwave sensors, or any combination thereof, disposes at one or more locations within the environment of interest. Security system 910 may be configured to detect intruders and/or threats based on the analysis and manipulation of such data. According to embodiments, security system 910 may be configured to grant and deny access to one or more locations within the environment of interest. Granting and denying access may comprise locking doors, unlocking doors, closing doors, opening doors, triggering alarms, shuttering windows, closing windows, opening windows, or any combination thereof, to name a few. In embodiments, security system 910 may be configured to grant or deny access based upon receiving, analyzing, and manipulating data from one or more cameras, biometric sensors, infrared sensor, RFID readers, card readers, or any combination thereof, to name a few.

Building systems 908 may include alarm system 912 configured to trigger, power, and/or cease one or more audible (e.g. siren, klaxon, bells, etc.), visual (lights, strobes, LEDs, display patterns, etc.), or tactile (vibrating alarms, motors, etc.) alarms located at one or more locations within the environment of interest. According to embodiments, alarm system 912 may be configured to control one or more alarms according to data received from any other building system 908 or aerosolized substance detection system 902. Building systems 908 may further include a heating, ventilation, and air conditioning (HVAC) system 914 configured to control, power, or modify the climate control, air filtration, heating, cooling, air scrubbing, exhaust, air circulation, humidity, temperature, or any combination thereof, of an environment of interest. For example, HVAC system 914 may be configured to control the filtration of odors, smoke, chemicals, contagions, bacteria, gasses, and/or any substance of interest discussed above with reference to FIG. 1 in one or more areas of the environment of interest. HVAC system 914 may be configured to filter substances from a location by activating or modifying the operation of one or more fans, ultraviolet light filters, high efficiency particulate air (HEPA) filters, electrostatic filters, washable filters, pleated filters, spun glass filters, media filters, forced-air systems, exhaust systems, or any combination thereof. In embodiments, HVAC system 914 may be configured to filter substances from a location based upon data received from any other building system 908 or aerosolized substance detection system 902.

According to embodiments, building systems 908 may include fire system 916 configured to control one or more fire prevention, fire suppression, and/or fire alarm systems of an environment of interest. For example, fire system 916 may be configured to control one or more smoke detectors, heat sensors, infrared sensors, carbon monoxide detectors, sprinklers, alarms, fire extinguishers, or any combination thereof. In embodiments, fire system 916 is configured to contact one or more emergency services (e.g., fire department, police department, emergency medical technicians, etc.), such as when a fire is detected. In embodiments, fire system 916 is configured to activate or modify one or more fire prevention, fire suppression, and/or fire alarm systems according to data received from any other building system 908 or aerosolized substance detection system 902. Building systems 908 further may include power system 918 configured to control electrical power to one or more locations within an environment on interest. Power system 918 may be configured to control, activate, or modify one or more electric meters, electrical generators, lighting systems, elevator systems, electrical circuits, backup power systems, emergency lighting systems, or any combination thereof, to name a few. In embodiments, power system 918 may be configured to control electrical power to one or more locations within an environment of interest according to data received from any other building system 908 or aerosolized substance detection system 902.

According to embodiments, each system building system 908 is configured to communicate with building management servers 922 and/or building management API 924 via the internet, ethernet, a wireless network, Bluetooth, Zigbee, ad-hoc network, or any combination thereof, to name a few. Additionally, or alternatively, building systems 908 can be configured to transmit any data from any building system 908 to building management servers 922 and/or building management API 924 via communication hub 920. Communication hub 920, similar or the same as communication hub 172, can be configured to be in communication with building systems 908, aerosolized substance detection system 902, building management servers 922, and building management API 924 and further be configured to facilitate communications between any combination thereof. In embodiments, building management servers 922 is configured to receive data from each building system 908 such as the status of systems, location of systems, measurements from sensors, locations of sensors, power consumption, fan speeds, current alarms, video, or any combination thereof. Building management servers 922 can be configured to generate one or more instructions for a respective building system 908 based upon received data. Instructions may comprise data instructing one or more systems to activate, deactivate, or modify the operation of one or more systems, sensors, motors, fans, alarms, or any combination thereof. For example, building management servers 922 may generate an instruction instructing HVAC system 914 to increase a fan speed and activate a HEPA filter based on received data. According to some embodiments, aerosolized substance detection system 902 may be in direct, or ad-hoc, communication with one or more building systems 908 such as by Bluetooth, RFID, NFC, Zigbee, wireless communications, wired communications, or any combination thereof. In some embodiments, communications between aerosolized substance detection system 902, building systems 908, building management servers 922, and/or building management API 924, may be encrypted such as by symmetric encryption and/or asymmetric encryption.

According to embodiments, aerosolized substance detection system 902 may be configured to detect one or more triggering events and/or detection events at one or more locations within an environment of interest. Aerosolized substance detection system 902 may include one or more entry units 904A-N, each similar or the same as entry unit 116, and one or more detection units 906A-N, each the similar or the same as detection unit 144. As discussed above with reference to FIGS. 1-6, each entry unit 904 is configured to detect a triggering event at one or more location in an environment of interest. For example, each entry unit may detect when a person has entered an environment of interest or an area proximate to the entry unit. In response to detecting the triggering event, each entry unit 904 may be configured to generate a detection signal that may be sent to one or more detection units 906A-N and/or building management servers 922. According to some embodiments, at least a portion of aerosolized detection system 802 may comprise a wearable device such as a sensor, user device, tablet, smart watch, smartphone, or any combination thereof, to name a few.

Further, as discussed above with reference to FIGS. 1-6, each detection unit 906 may be configured to measure, in response to the detection signal, a quantity (i.e., particle count), size, structure, dispersion, or any combination thereof, of one or more substances within an environment or interest or proximate to the detection unit. For example, a detection unit 906 may be configured to detect a particle count of a discouraged substances within an environment of interest. In embodiments, each detection unit 906 may transit any measurements to building management servers 922. Additionally, each detection unit 906 may transmit identification information related to the detection unit such as a physical location, a location within an environment of interest, a MAC address, an IP address, or any combination thereof.

According to some embodiments, and as discussed above with reference to FIGS. 1-6, each detection unit 906 may further be configured to determine that a detection event has occurred such as by determining a taken measurement to a threshold value. For example, a detection unit may compare a taken measurement of a particle court for a discouraged substance to a threshold value. Each detection unit 906 may further be configured to transmit a signal indicating that a detection event has occurred to building management servers 922. In embodiments, building management servers 922 may be configured to generate one or more instructions for a respective building system 908 based upon measurements received from aerosolized substance detection system 902, received detection signals or signals indicating a detection event has occurred, and/or determined triggering events or detection events. For example, building management servers 922 may receive a detection signal indicating that a certain particle count of a contagion has been detected within a location of the environment of interest. In response, building management servers 922 may be configured to generate an instruction instructing HVAC system 914 to activate a HEPA filter in the same location. In some embodiments, aerosolized substance detection system 902 may directly communicate with one or more building systems 908 to modify a building system 908 when a detection event is determined.

Building management servers 922 may include one or more servers which may comprise any computing device as described in this disclosure, including without limitation a microcontroller, microprocessor, digital signal processor (DSP) and/or system on a chip (SoC) as described in this disclosure. Each server of building management servers 922 may include, be included in, and/or communicate with a user device such as a mobile telephone or smartphone. Any server of building management servers may include a single computing device operating independently, or may include two or more computing devices operating in concert, in parallel, sequentially or the like; two or more computing devices may be included together in a single computing device or in two or more computing devices. Any server of building management servers 922 may interface or communicate with one or more additional devices as described below in further detail via a network interface device. Network interface devices may be utilized for connecting a server to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Any server of building management servers 922 may include but is not limited to, for example, a computing device or cluster of computing devices in a first location and a second computing device or cluster of computing devices in a second location. Any server of building management servers 922 may include one or more computing devices dedicated to data storage, security, distribution of traffic for load balancing, and the like. Any server of building management servers 922 may distribute one or more computing tasks as described below across a plurality of computing devices, which may operate in parallel, in series, redundantly, or in any other manner used for distribution of tasks or memory between computing devices.

Building management API 924 comprises an application programming interface configured to interact with building management system 900. In embodiments, building management API 924 can be configured to run a user device the same or similar as user device 384, and is configured to display, modify, store, transmit, and/or manipulate data to and from building management servers 922. For example, security API may be configured to display one or more statues from any building system 908 and may also be configured to set threshold values for trigger and detection events as discussed above with reference to FIGS. 1-6.

In embodiments, building management API 924 may be configured to receive one or more interactions. Interactions may comprise a swipe on a touchscreen, a tap on a touchscreen, text entry, mouse movements, or any combination thereof, to name a few. According to embodiments building management API 924 may be configured to generate one or more instructions from one or more building systems 908 according to received interactions. For example, building management API 924 may be generate instructions instructing the activation of one or more fans and air filtration system in response to received interactions.

According to embodiment, building management servers 922 and/or building management API 924 may be configured to determine a specification of one or more locations within the environment of interest. A "specification" as used herein, is data including the presence, model, operation, obsolescence, current performance, historical performance over a predetermined period of time, and/or maintenance of one or more building systems 908 at the one or more locations. For example, a specification can include data indicating a number of air filters in a location, their model, the last time they were maintained, and a historical performance from a prior week. In embodiments, building management servers 922 and/or building management API 924 may be configured to compare a specification of a location to a threshold value, building code, technology standard, predetermined data, or any combination thereof, to name a few. Based upon this comparison, building management servers 922 and/or building management API 924 may determine whether the location meets the specification. For example, building management servers 922 and/or building management API 924 may compare the air filters present in a location to a building code to determine whether the location meets the specification. According to embodiments, when building management servers 922 and/or building management API 924 determines that a location does not meet a specification, building management servers 922 and/or building management API 924 may generate a notification indicating that the location does not meet the specification. The notification may be displayed by building management API 924 or any user device as discussed above.

Referring now to FIG. 9B, an example implementation of aerosolized substance detection system 902 in building management system 900 is presented. According to an example embodiment, building management system 900 can include at least a portion of one or more building systems 908 disposed in an environment of interest 928. For example, building management system 900 may include an air filter from HVAC system 914, a siren from alarm system 912, one or more doors controlled by security system 910, or any combination thereof disposed in environment of interest 928. Environment of interest 928 can include any environment configured for the containment of animals such as, for example, a room or area in a kennel, laboratory, zoo, cargo hold, aquarium, university, comparative medicine facility, veterinary hospital, or veterinary clinic, to name a few.

Environment of interest 928 can include one or more animal containment units 930A-H. An animal containment unit 930 may comprise a habitat, housing, crate, cage, tank, terrarium, and/or area configured to contain one or more animals. While in the illustrative embodiment of FIG. 9B, eight animal containment units are presented, in other embodiments, any number may be used. Aerosolized substance detection system 902 is configured to monitor air quality proximate or around one or more animal containment units 930A-H such. For example, aerosolized substance detection system 902 may be configured to monitor air quality by taking a measurement of a vapor cloud 926 that is proximate or near animal containment units 930A and 930E.

In an example embodiment, detection unit 906 may be configured to periodically take a measurement of particle cloud 926 as discussed above with reference to FIGS. 1-6. In some embodiments, detection unit 906 may determine that a detection event has occurred based on the taken measurement and may transmit a signal indicating a detection event has occurred to building management servers 922. In other embodiments, the taken measurement may be transmitted to building management servers 922 which may, in turn, determine that a detection event has occurred based on the taken measurement. According to embodiments, building management servers 922 may be configured to instruct a building system 908 to modify in response to receiving a signal indicating a detection event has occurred or determining a detection event has occurred. For example, building management server may instruct alarm system 922 to activate an alarm, instruct HVAC system 914 to activate an air filter, and/or instruct security system 910 to lock one or more doors in response to receiving a signal indicating a detection event has occurred or determining a detection event has occurred. In some embodiments, aerosolized substance detection system 902 may directly communicate with one or more building systems 908 to modify a building system 908 when a detection event is determined.

FIG. 10 is a flowchart of an example method for adjusting a building system based upon a detection event. At 1005, at least a portion of aerosolized substance detection system 902 is active, such as an entry unit 904. At 1010, at least a portion of aerosolized substance detection system 902 may determine whether or not a triggering event has been detected. For example, as discussed above with reference to FIGS. 1-6, entry unit 904 may determine that a person has been detected entering a location near or proximate to the entry unit 904. If no triggering event was detected, then the system goes to 1005. Otherwise, the system moves to 1015. At 1015, aerosolized substance detection system 902 is configured to take a reading or measurement of a substance of interest as discussed above with reference to FIGS. 1-6. For example, a detection unit 906 of aerosolized substance detection system 902 may be configured to measure the particle count of a contagion. In embodiments, detection unit 906 may transmit data representing the measurement to building management server 922.

At 1020, the reading taken of the substance of interest may be compared to a threshold value. Comparing the reading to the threshold may be performed by a detection unit 906, aerosolize substance detection system 902, and/or building management servers 922. In embodiments, the reading may be compared to the threshold value to determine whether the threshold is exceeded. For example, a particle count of a contagion may be compared to a threshold value to determine whether the particle count is greater than the threshold. If the threshold has been exceeded the system moves to 1025, otherwise the system moves to 1005.

At 1025, building management servers 922 may determine if any mitigation action can be taken to alleviate or remedy the detection event. A mitigation action comprises the activation, deactivation, or modification of one or more building systems 908 that can address the detection event. For example, a mitigation action comprising the activation of a sprinkler system may address a detection event indicating smoke. Additionally, for example, a mitigation action comprising activating a HEPA filter at a location may address a detection event indicating a contagion in the air. If no mitigation activation is available, the system moves on to 1030, otherwise the system moves on to 1035. At both 1030 and 1035, the system generates an alert comprising data indicating a detection event has occurred. In some embodiments, the alert may further indicate whether a mitigation action is available for the detection event. According to embodiments, the alert may be transmitted to building management servers 922 and may be displayed in building management API 924 or any user device as discussed above. From 1030, the system moves to 1005 and from 1035, the system moves to 1040.

At 1040, the determined mitigation action is transmitted to the respective building system 908. For example, a mitigation action comprising activating a HEPA filter at a location is transmitted to HVAC system 914. At 1045, the respective building system 908 modifies a system according to the mitigation action. Modifying the system comprises activating, deactivating, and/or modifying one or more systems according to the mitigation action. For example, activating one or more HEPA filters in a location indicated by the mitigation action.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 11:
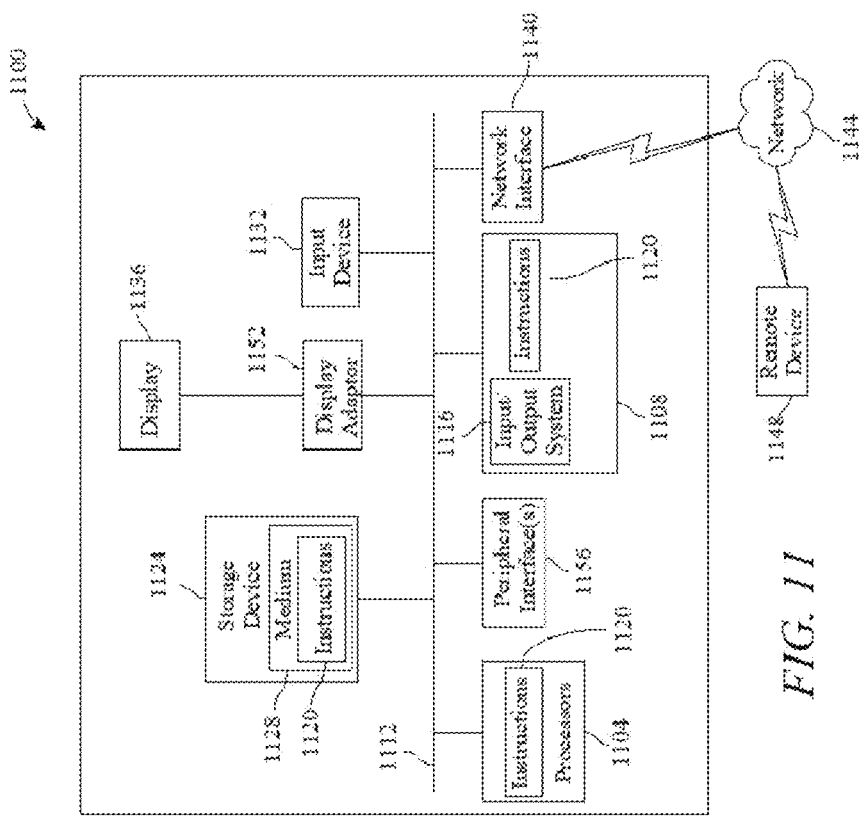
FIG. 11 is a block diagram illustrating a computing device in the example form of a computer system, according to embodiments.

FIG. 11 shows a diagrammatic representation of one embodiment of a computing device in the exemplary form of a computer system 1100 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1100 includes a processor 1104 and a memory 1108 that communicate with each other, and with other components, via a bus 1112. Bus 1112 may include any of several types of bus structures including, but not limited to, a memory bus, a memory controller, a peripheral bus, a local bus, and any combinations thereof, using any of a variety of bus architectures.

Processor 1104 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 1104 may be organized according to Von Neumann and/or Harvard architecture as a non-limiting example. Processor 1104 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC).

Memory 1108 may include various components (e.g., machine-readable media) including, but not limited to, a random-access memory component, a read only component, and any combinations thereof. In one example, a basic input/output system 1116 (BIOS), including basic routines that help to transfer information between elements within computer system 1100, such as during start-up, may be stored in memory 1108. Memory 1108 may also include (e.g., stored on one or more machine-readable media) instructions (e.g., software) 1120 embodying any one or more of the aspects and/or methodologies of the present disclosure. In another example, memory 1108 may further include any number of program modules including, but not limited to, an operating system, one or more application programs, other program modules, program data, and any combinations thereof.

Computer system 1100 may also include a storage device 1124. Examples of a storage device (e.g., storage device 1124) include, but are not limited to, a hard disk drive, a magnetic disk drive, an optical disc drive in combination with an optical medium, a solid-state memory device, and any combinations thereof. Storage device 1124 may be connected to bus 1112 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1124 (or one or more components thereof) may be removably interfaced with computer system 1100 (e.g., via an external port connector (not shown)). Particularly, storage device 1124 and an associated machine-readable medium 1128 may provide nonvolatile and/or volatile storage of machine-readable instructions, data structures, program modules, and/or other data for computer system 1100. In one example, software 620 may reside, completely or partially, within machine-readable medium 1128. In another example, software 620 may reside, completely or partially, within processor 1104.

Computer system 1100 may also include an input device 1132. In one example, a user of computer system 600 may enter commands and/or other information into computer system via input device 1132. Examples of an input device 1132 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera 180, a video camera 180), a touchscreen, and any combinations thereof. Input device 1132 may be interfaced to bus 1112 via any of a variety of interfaces (not shown) including, but not limited to, a serial interface, a parallel interface, a game port, a USB interface, a FIREWIRE interface, a direct interface to bus 1112, and any combinations thereof. Input device 1132 may include a touch screen interface that may be a part of or separate from display 1136, discussed further below. Input device 1132 may be utilized as a user selection device for selecting one or more graphical representations in a graphical interface as described above.

A user may also input commands and/or other information to computer system 600 via storage device 1124 (e.g., a removable disk drive, a flash drive, etc.) and/or network interface device 1140. A network interface device, such as network interface device 640, may be utilized for connecting computer system 1100 to one or more of a variety of networks, such as network 1144, and one or more remote devices 1148 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1144, may employ a wired and/or a wireless mode of communication. In general, any network topology may be used. Information (e.g., data, software 1120, etc.) may be communicated to and/or from computer system 1100 via network interface device 1140.

Computer system 1100 may further include a video display adapter 1152 for communicating a displayable image to a display device, such as display device 1136. Examples of a display device include, but are not limited to, a liquid crystal display (LCD), a cathode ray tube (CRT), a plasma display, a light emitting diode (LED) display, and any combinations thereof. Display adapter 1152 and display device 1136 may be utilized in combination with processor 1104 to provide graphical representations of aspects of the present disclosure. In addition to a display device, computer system 1100 may include one or more other peripheral output devices including, but not limited to, an audio speaker, a printer, and any combinations thereof. Such peripheral output devices may be connected to bus 1112 via a peripheral interface 1156. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A building management system, comprising:
   a trigger sensor configured to enter a scanning mode based on detecting a triggering event at a first location of an environment;
   a detection unit disposed at the first location of the environment, the detection unit comprising:
      a particle sensor configured to detect a particle count of a substance proximate to the first location of the environment; and
      a detection unit housing configured to enclose at least a portion of the particle sensor,
      wherein the detection unit is configured to:
         periodically check whether the trigger sensor has entered the scanning mode; and
         provide power to the particle sensor in response to determining the trigger sensor has entered the scanning mode;
   an HVAC system disposed proximate to the first location of the environment, the HVAC system comprising an air filter configured to filter the substance; and
   a server communicatively connected to the detection unit and the HVAC system and configured to activate the air filter.

2. The system of claim 1, wherein the detection unit is further configured to:
   determine a detection event based upon the particle count.

3. The system of claim 2, wherein the server is further configured to activate an air filter system based upon the detection event.

4. The system of claim 1, wherein the server is configured to determine a detection event by comparing the particle count to a predetermined threshold.

5. The system of claim 3, wherein the server is further configured to compare the air filter to a specification.

6. The system of claim 5, wherein the server is further configured to generate a notification based upon the comparison of the air filter to the specification.

7. The system of claim 1, wherein the server is configured to activate an alarm based upon the particle count.

8. The system of claim 1, wherein the particle sensor is configured to detect the particle count of a contagion.

9. The system of claim 1, wherein the server is communicatively connected to the detection unit and the HVAC system via a communication hub.

10. The system of claim 1, wherein the triggering event comprises a presence of the substance in the first location of the environment.

* * * * *